United States Patent
Chen et al.

(10) Patent No.: US 6,265,572 B1
(45) Date of Patent: Jul. 24, 2001

(54) PYRROLIDINCARBONYLAMINO CYCLIC DISULFIDE ANTI-INFLAMMATORY AGENTS

(75) Inventors: Li Chen, Westfield; Nader Fotouhi, Chatham, both of NJ (US); David Young Jackson, San Bruno, CA (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/548,992

(22) Filed: Apr. 14, 2000

Related U.S. Application Data

(60) Provisional application No. 60/130,215, filed on Apr. 20, 1999.

(51) Int. Cl.$^7$ .................. C07D 225/04; C07D 267/22
(52) U.S. Cl. ............................ 540/453; 540/454
(58) Field of Search ..................... 540/453, 454

(56) References Cited

FOREIGN PATENT DOCUMENTS

WO 92/00995   1/1992  (WO).

OTHER PUBLICATIONS

Jackson, et al. J. Med. Chem. vol. 40, No. 21, pp. 3359–3368 (1997).
Nowlin, et al. J. Biol. Chem. vol. 268, pp. 20352–20359 (1993).
CA 133:171743 (2000).

*Primary Examiner*—Bruck Kifle
(74) *Attorney, Agent, or Firm*—George W. Johnston; William H. Epstein

(57) ABSTRACT

Compounds of the formula:

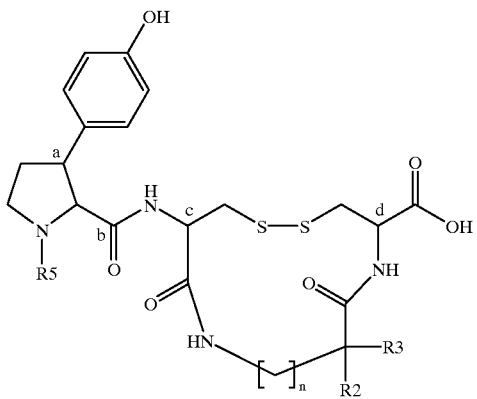

are described which have activity as anti-inflammatory agents. Cyclic disulfide compounds are provided which inhibit of binding of cells to endothelium. Such compounds are useful for treating inflammatory diseases, such as asthma, whose symptoms and/or damage are related to the binding of cell adhesion molecules to integrin expressing cells.

26 Claims, No Drawings

PYRROLIDINCARBONYLAMINO CYCLIC DISULFIDE ANTI-INFLAMMATORY AGENTS

This application claims priority under 35 U.S.C. § 119(e) of provisional application(s) Serial No. 60/130,215, filed Apr. 20, 1999.

FIELD OF THE INVENTION

This invention relates generally to pyrrolidinyl cyclic disulfide compounds which are useful therapeutic agents for the treatment of inflammatory diseases.

BACKGROUND OF THE INVENTION

Vascular cell adhesion molecule-1 (VCAM-1), a member of the immunoglobulin (Ig) supergene family, is expressed on activated endothelium. The integrin VLA-4 ($a_4\beta_1$), is the principal receptor for VCAM-1. VLA-4 is expressed on many cell types including circulating lymphocytes, eosinophils, basophils, and monocytes. VCAM-1 also binds to a second integrin LPAM-1 (Peyer's patch adhesion molecule) with is expressed on B and T-cells. The integrin LPAM-1 can also bind with another cell adhesion molecule called mucosal addressing cell adhesion molecule (MadCAM). Binding of the integrins VLA-4 and LPAM-1 to cell adhesion molecules VCAM-1 or MadCAM normally allows the passage of macromolecules and circulating cells from blood to tissue. However, binding of integrins to cell adhesion molecules can result in undesirable inflammation wherein the above cell types infiltrate tissue and cause tissue damage.

Therefore, cell adhesion molecule/integrin antagonists which inhibit the binding of integrins to cell adhesion molecules are able to prevent undesirable inflammation. For example, such antagonists are needed to prevent tissue damage caused by inflammatory bowel disease, T-cell emigration in arthritis, eosinophil accumulation and bronchoconstriction in asthma, and prolongation of the survival time of tissue allografts.

SUMMARY OF THE INVENTION

In accordance with this invention, it has been discovered that compounds selected from the group consisting of cyclic disulfide compounds of the formula:

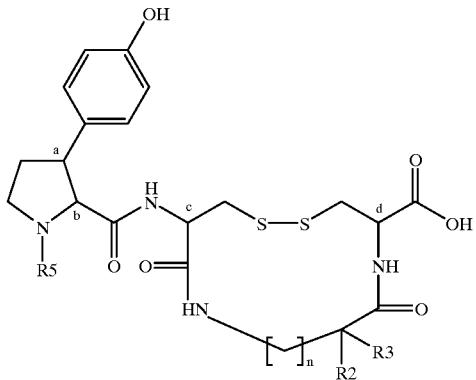

wherein $R_2$ and $R_3$ are each independently lower alkyl, or taken together with their attached carbon atom form an aliphatic carbocyclic ring containing 4 to 6 carbon atoms; $R_5$ is hydrogen, lower alkyl, R—$SO_2$—, $R_6$—$(CH_2)_m$—CO— or $R_8$—X—$(CH_2)_y$—CO—; R is lower alkyl; $R_6$ and $R_8$ are hydrogen or lower alkyl; X is —O— or —NH—; m is an integer of from 1 to 7, y is an integer of from 0 to 7, and n is an integer of from 1 to 3; with a, b, c, and d denoting asymmetric carbon atoms; and hydrolyzable esters or ethers thereof.

The compounds of the present invention are effective anti-inflammatory agents. In accordance with the present invention, the cyclic disulfide compounds combat inflammation by inhibiting adhesion of α4 integrin expressing cells to endothelium. The general mechanistic action of the cyclic disulfide compounds is the inhibition of binding of α4 integrin expressing cells to cell adhesion molecules of the endothelium. This compounds may also inhibit local activation of such cells at the site of inflammation, such as in the lung. The compounds of the present invention are particularly useful for the treatment of inflammation such as inflammation associated with chronic inflammatory diseases which include pulmonary inflammation, asthma, rheumatoid arthritis, multiple sclerosis (MS), and inflammatory bowel disease (IBD).

DETAILED DESCRIPTION OF THE INVENTION

As used throughout this application, the term "lower alkyl" includes both straight chain and branched chain alkyl groups having from 1 to 7 carbon atoms, such as methyl, ethyl and propyl, preferably methyl. As used herein, the term "lower alkoxy" comprehends a straight chain or branched-chain alkoxy group having from 1 to 7 carbon atoms, such as methoxy, ethoxy, n-propoxy, isopropoxy, n-butoxy, tert-butoxy and the like. As also used herein, the term "lower alkanoic acids" comprehends an alkanoic acid of 2 to 7 carbon atoms such as propionic acid and acetic acid. As further used herein, the term "halogen" or "halo", unless otherwise stated, comprehends fluorine, chlorine, bromine and iodine.

The term "substituted lower alkyl" means a lower alkyl group substituted by one or more groups selected independently from hydroxy, halogen, cyano, lower alkoxy, lower alkanoyl, lower alkylthio, lower alkyl sulfinyl, lower alkyl sulfonyl, and substituted amino. Examples of substituted lower alkyl groups include 2-hydroxyethyl, 2,2,2,-trifluroethyl, cyanomethyl, and 2-nitropropyl.

The term "lower alkanoyl" or "acyl" denotes a radical derived from an aliphatic carboxylic acid of 2 to 7 carbon atoms, for example, acetyl, propionyl and the like. The term "acyl" besides meaning "lower alkanoyl" also includes aroyl such as benzoyl.

As also used herein, the term "aryl" signifies mononuclear aromatic hydrocarbon groups such as phenyl, tolyl, etc., which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be substituted with one or more of the aforementioned groups. The preferred aryl groups are the substituted and unsubstituted mononuclear aryl groups, particularly phenyl. The term "aralkyl" denotes an alkyl group, where alkyl is lower alkyl, in which one of the hydrogen atoms has been replaced by an aryl group, examples of aralkyl groups are benzyl, 2-phenylethyl, 3-phenylpropyl, 4-chloro-benzyl, 4-methoxybenzyl and the like.

As used herein, the term "hydrolyzable ester or ether group" designates any ester or ether which can be hydrolyzed to yield a hydroxyl group and/or a carboxyl group. Exemplary ester groups useful for this purpose are those in which the acyl moiety is derived from a lower alkanoic, an aryl lower alkanoic, or a lower alkane dicarboxylic acid. Among the activated acids which can be utilized to form such ester groups are the acid anhydrides and the acid halides, preferably acid chlorides or acid bromides derived from aryl or lower alkanoic acids. Examples of anhydrides include acetic anhydride, caproic anhydride, benzoic acid anhydrides, lower alkane dicarboxylic acid anhydrides, e.g., succinic anhydride. In addition, hydrolyzable esters can be formed from chloroformates, e.g., trichloroethylchloroformate.

A suitable ether protecting group is, for example, the tetrahydropyranyl ether or 4-methoxy-5,6-dihydro-2H-pyranyl ether. Others are arylmethyl ethers such as benzyl, benzhydryl, or trityl ethers or α-lower alkoxy lower alkyl ether, for example, methoxymethyl or allylic ethers, or alkyl silyl ethers such as trimethyl silyl ether Alternatively, the term "hydrolyzable ester group" designates an ester which can be hydrolyzed to yield a carboxyl group. Typically, the alkoxyl moiety is derived from a lower alkanol or substituted lower alkanol. Among the alkanols which can be utilized to form such ester groups are substituted or unsubstituted primary, secondary and tertiary alkanols, such as ethanol, methanol, iso-propanol, tert-butanol and 2-(dimethyl amino)ethanol.

The term "thio protecting group" designates any group which can be cleaved to yield a free thio group. Among the preferred thio protecting groups are tri-arylmethane, tri-alkylmethane, aralkyl groups such as benzyl. Preferred acyl groups are lower alkanoyl and aroyl, particularly, benzoyl. Generally, it is preferred to utilize an acid cleavable thio protecting group for example a tri-aryl methyl group such as a trityl group being especially preferred.

The term "amino protecting group" designates any group which can be cleaved to yield a free amino group. The amino protecting group can be any conventional amino protecting group utilized in peptide synthesis. Generally, preferred amino protecting groups are those which are cleavable under mildly acidic conditions of from about pH 2.0 to 3.0. Particularly, preferred amino protecting groups are tertiary lower alkyl, lower alkyl and tri-lower alkyl methyl groups.

The term "pharmaceutically acceptable salts" is used to include salts with both inorganic and organic pharmaceutically acceptable salts such as hydrochloric acid, hydrobromic acid, nitric acid, sulfuric acid, phosphoric acid, citric acid, formic acid, maleic acid, acetic acid, succinic acid, tartaric acid, methanesulfonic acid, para toluene sulfonic acid and the like. Such salts can be formed quite readily by those skilled in the art using standard techniques.

The present invention relates to compounds selected from the group consisting of compounds of the formula:

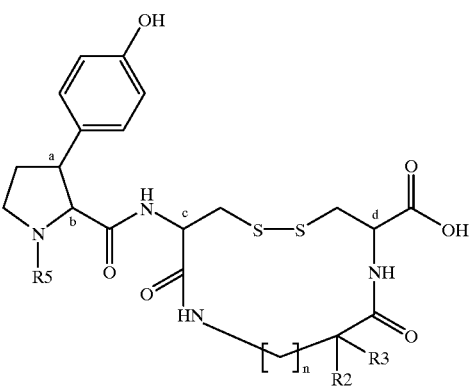

wherein $R_2$ and $R_3$ are each independently lower alkyl, or taken together with their attached carbon atom form an aliphatic carbocyclic ring containing 4 to 6 carbon atoms; $R_5$ is hydrogen, lower alkyl, R—SO$_2$—, $R_6$—(CH$_2$)$_m$—CO— or $R_8$—X—(CH$_2$)$_y$—CO—; R is lower alkyl; $R_6$ and $R_8$ are hydrogen or lower alkyl; X is —O— or —NH—; m is an integer of from 1 to 7, y is an integer of from 0 to 7, and n is an integer of from 1 to 3; with a, b, c, and d denoting asymmetric carbon atoms; and hydrolyzable esters or ethers thereof.

$R_2$ and $R_3$ together with their attached carbon form a cycloalkane or a cycloalkene group containing from 4 to 7 carbon atoms, such as, cyclopentane, cyclopentene, cyclobutane, cyclobutene, cyclohexane or cyclohexene.

The compounds of the present invention are effective anti-inflammatory agents. In accordance with the present invention the cyclic disulfide compounds combat inflammation by inhibiting adhesion of α4 integrin expressing cells to cell adhesion molecules of the endothelium. The compounds of the present invention are particularly useful therapeutic agents for the treatment of inflammation associated with chronic inflammatory diseases such as, for example, rheumatoid arthritis, multiple sclerosis (MS), and inflammatory bowel disease (IBD). The compounds of the invention are also particularly useful in the treatment of diseases which involve pulmonary inflammation, such as asthma.

In the pictorial representation of the compounds given throughout this application, a thickened tapered line (▼) indicates a substituent which is above the plane of the ring to which the asymmetric carbon belongs, a dotted line (—) indicates a substituent which is below the plane of the ring to which the asymmetric carbon belongs, and a wavy line (~) indicates a substituent which can be either above or below the plane of the molecule. It is to be understood that the pictorial representation of the compounds given throughout the specification are set forth for convenience and are to be construed as inclusive of other forms including stereoisomers, enantiomers and racemates and are not to be construed as limited to the particular form shown.

Compounds of formula 1 and pharmaceutically acceptable salts thereof, as well as intermediates of compounds of formula 1 exhibit stereoisomerism. The compounds of this invention can be any isomer of the compound of formula 1 or mixtures of these isomers. The compounds and intermediates of the present invention having one or more asymmetric carbon atoms may be obtained as racemic mixtures of stereoisomers which can be resolved, at the appropriate steps in the process of this invention by methods well known in the art to obtain a given stereoisomer or pure enantiomer having a desired stereoconfiguration. Alternatively, the desired isomers may be directly synthesized by methods known in the art.

Asymmetric carbon atoms in the compounds of the present invention are denoted as a, b, c and d. The stereoconfigurations of each of the asymmetric carbon atoms denoted as a, b, c, and d can be designated according to the particular stereoisomer it represents. Compounds of the present invention include those compounds wherein the carbon atom denoted as "a" has the S, R, or R,S-configuration; the carbon atom denoted as "b" has the S, R, or R,S-configuration; the carbon atom denoted as "c" has the S, R, or R,S-configuration; and the carbon atom denoted as "d" has the S, R, or R,S-configuration.

The preferred stereo configuration of the compounds of the present invention are the pure stereo isomers of the compounds of formula 1. Compounds having this preferred stereo configuration are compounds of the formula 1a:

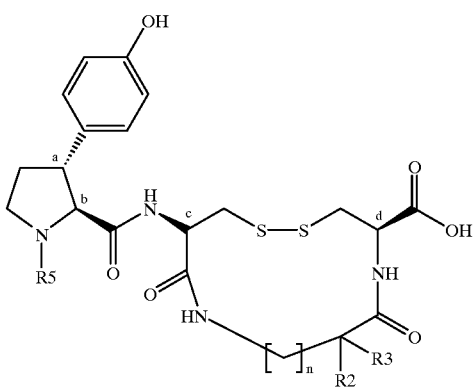

Ia wherein $R_2$ and $R_3$ in the above compound taken together with the attached carbon atom form a cyclopentane ring, the preferred configuration is a compound of the formula:

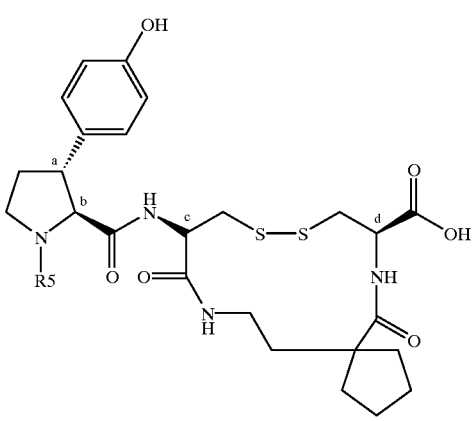

Ib

The compounds of formula 1 and especially the analog derived from the pure (+)-trans isomers of the pyrrolidine of the compounds of formula 1 exhibit great potency as anti-inflammatory agents. A means for determining the potency of these anti-inflammatory agents is by evaluating their ability to inhibit binding of the integrin VLA-4 to the cell adhesion molecule VCAM-1. For example, the potency of the compounds herein can be determined with respect to the concentration of the compound at 50% inhibition of VCAM/VLA4 binding ($IC_{50}$) as measured by VLA-4/VCAM-1 binding assay. The compounds of the present invention, especially the substantially pure (+)-trans isomeric forms, i.e., (+)-trans isomers that contain less than about 5% of corresponding stereoisomers, exhibit higher potency than previously known VCAM/VLA4 antagonists.

In accordance with the present invention, any conventional method known in the art can be used to determine inhibition of VCAM-1/VLA-4 binding. For example, a solid-phase dual antibody ELISA or Ramos cell-based screening assay can be utilized to determine inhibition of VCAM-1/VLA-4 binding.

Compounds of formula 1 which are especially preferred are:

(8R,13R)-13-[[[1-acetyl-1-(R)-(4-hydroxyphenyl)-2-(S)-pyrrol-dinyl]carbonyl]amino]-6,14-dioxo-10,11-dithia-7,15-diazaspiro[4.1 2]heptadecane-8-carboxylic acid;

(9R,14R)-14-[[[1-acetyl-3-(R)-(4-hydroxyphenyl)-2-(S)-pyrrolidinyl]carbonyl]amino]-7,15-dioxo-11,12-dithia-8,16-diazaspiro[5.12]octadecane-9-carboxylic acid;

(8R,13R)-1-3-[[[1-methylsulfonyl-3-(R)-(4-hydroxyphenyl)-2-(S)pyrrolidinyl]carbonyl]amino]-6,14-dioxo-10,11-dithia-7,15-diazaspiro[4.12]heptadecane-8-carboxylic acid;

(8R,13R)-1-3-[[[1-(2,2-dimethyl-1-oxopropyl)-3-(R)-(4-hydroxyphenyl)-2-(S)-pyrrolidinyl]carbonyl]amino]-6,14-dioxo-10,11-dithia-7,15-diazaspiro[4.12]heptadecane-8-carboxylic acid; and (8R,13R)-13-[[[3-(R)-(4-hydroxyphnyl)-2-(S)-pyrrolidinyl]carbonyl]amino]-6,4-dioxo-10,11-dithia-7,15-diazaspiro[4.12]heptadecane-8-carboxylic acid.

The compounds of the invention can be administered orally, rectally, or parentally, e.g., intravenously, intramuscularly, subcutaneously, intrathecally or transdermally; or sublingually, or as opthalmalogical preparations, or as an aerosol for the treatment of pulmonary inflammation. Capsules, tablets, suspensions or solutions for oral administration, suppositories, injection solutions, eye drops, salves or spray solutions are examples of administration forms.

Intravenous, intramuscular, oral or inhalation administration is a preferred form of administration. The dosages in which the compounds of the invention are administered in effective amounts depend on the nature of the specific active ingredient, the age and the requirements of the patient and the mode of administration. Dosages may be determined by any conventional means, e.g., by dose-limiting clinical trials. Thus, the invention further comprises a method of treating a host suffering from a disease in which VCAM-1 or fibronectin binding to VLA-4-expressing cells is a causative factor in the disease symptoms or damage by administering an amount of a compound of the invention sufficient to inhibit VCAM-1 or fibronectin binding to VLA-4-expressing cells so that said symptoms or said damage is reduced. In general, dosages of about 0.1–100 mg/kg body weight per day are preferred, with dosages of 1–25 mg/kg per day being particularly preferred, and dosages of 1–10 mg/kg body weight per day being especially preferred.

The invention further comprises pharmaceutical compositions which contain a pharmaceutically effective amount of a compound of the invention and a pharmaceutically acceptable carrier. Such compositions may be formulated by any conventional means. Tablets or granulates can contain a series of binders, fillers, carriers or diluents. Liquid compositions can be, for example, in the form of a sterile water-miscible solution. Capsules can contain a filler or thickener in addition to the active ingredient. Furthermore, flavor-improving additives as well as substances usually used as preserving, stabilizing, moisture-retaining and emulsifying agents as well as salts for varying the osmotic pressure, buffers and other additives can also be present.

The previously mentioned carrier materials and diluents can comprise any conventional pharmaceutically acceptable organic or inorganic substances, e.g., water, gelatine, lactose, starch, magnesium stearate, talc, gum arabic, polyalkylene glycols and the like.

In accordance with the present invention, compounds of formula 1 are prepared by reacting the cyclic peptide core compound of formula 13

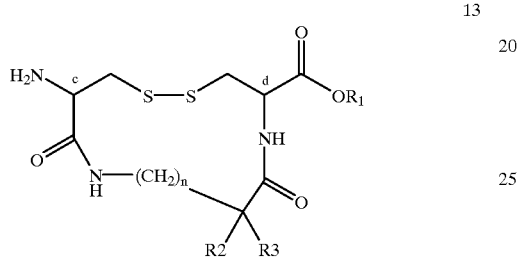

wherein $R_1$ with its attached oxygen forms a hydrolyzable ester group;

and R2 and R3 are as above with the compound of formula 19

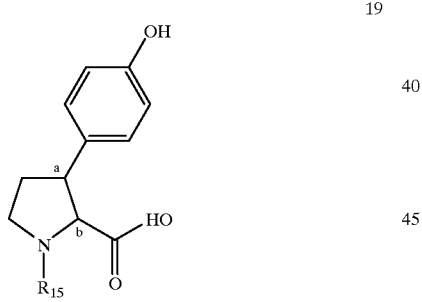

wherein $R_{15}$ is lower alkyl, R—SO$_2$—, $R_6$—(CH$_2$)$_m$—CO— or $R_8$—X—(CH$_2$)$_y$—CO— and R, $R_6$ and $R_8$ are as above.

The cyclic peptide core 13 suitable for the preparation of compounds of this invention can be prepared by reacting the compounds of formulas 2 and 3 according to the following Reaction Scheme I.

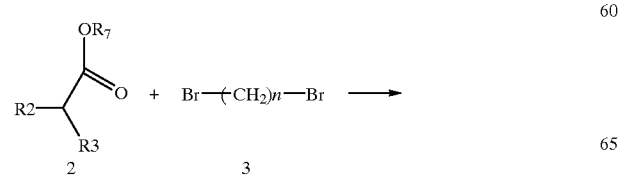

wherein $R_1$ with its attached oxygen forms a hydrolyzable ester group; $R_2$ and $R_3$ are as above; $R_7$ with its attached oxygen forms a hydrolyzable ester group; $R_9$ is an amino protecting group; $R_{10}$ and $R_{10'}$ are thio protecting groups; and n is as above.

$R_7$ in the compound of formula 2 is formed from the corresponding acid by protecting the free carboxy group of this acid through esterification. $R_7$ is preferably lower alkyl such as a methyl group. In preparing the compound of formula 2, the corresponding free acid in the compound of formula 2 is reacted with an alkyl halide to form the protective ester. Any conventional method of converting the corresponding free acid group of formula 2 to a standard hydrolyzable ester protecting group can be utilized.

In Reaction Scheme I, the ester of formula 2 is alkylated by reacting the compound of formula 2 with the dibromoalkane of formula 3. This alkylation is conveniently carried out by treating the ester of formula 2 with a strong base, for example lithium diisopropylamide, in an inert solvent, for example THF maintained at a low temperature, typically −40 to −78° C. and then reacting the reaction mixture with the dibromoalkane of formula 3 at this temperature to provide the bromide of formula 4. The bromide of formula 4 is reacted with an alkali metal azide to form the azide of formula 5. Any conventional means of converting a halide to an azide group can be utilized in this step of the reaction. For example, sodium azide in a suitable inert solvent such as DMF at a temperature of from room temperature to 80° C. yields the azide of formula 5.

The azide of formula 5 is converted to the compound of formula 6 by hydrolysis of the ester protecting group formed by $R_7$. This hydrolysis to produce the compound of formula 6, which is the corresponding free acid of the azide of formula 5, can be carried out by any conventional means of ester hydrolysis. For example, hydrolysis of the ester group of formula 5 can be accomplished by treatment with an excess of lithium hydroxide in aqueous methanol at a temperature of room temperature to the reflux temperature of the solvent, yielding the acid of formula 6.

In the next step of the reaction, the free acid of formula 6 is reacted with the amine of formula 7 to form an amide linkage between the free acid group of formula 6 and the free amino group of formula 7 thereby obtaining the azide compound of formula 8. In forming the compound of formula 8, any conventional method of amide formation can be utilized in carrying out this reaction. The condensation reaction of the compounds of formulas 6 and 7 is preferably carried out using conventional coupling reagents as employed in peptide chemistry, for example, HBTU in the presence of a tertiary base such as diisopropylethylamine in a suitable solvent, for example, DMF at room temperature.

In the compound of formula 7, the carboxyl group is protected by $R_1$. Use of a tert-buityl group is preferred because it can be easily removed in subsequent reactions in this scheme without affecting other protecting groups on the ring. Also in the compound of formula 7, $R_{10}$ is a thio protecting group. As described hereinabove, any suitable thio protecting group may be utilized.

Compound 7 having an asymmetric carbon atom denoted as "d" can have a specific stereoconfiguration. On the other hand compound 7 can be a mixture of stereoisomers. The stereoconfiguration of compound 7 is carried out throughout the entire reaction scheme. Therefore, the stereoconfiguration of the final product, compound 1 depends on the stereoconfiguration of compound 7. That is, at the asymmetric carbon atom denoted as "d", Compound 1 will have the same specific stereoconfiguration of compound 7, or if compound 7 is a mixture of stereoisomers then compound 1 will be produced as a mixture of stereoisomers.

The compound of formula 8 is converted to the compound of formula 9 by reduction of the azide group to the corresponding primary amine. Any conventional method of reducing an azide to the corresponding primary amine can be utilized. Generally, reduction of the azide 8 to form the amine of formula 9 is carried out using conventional reducing agents, preferably, a phosphine such as trimethyl- or triphenylphosphine in a suitable inert solvent such as dichloromethane at room temperature.

In the next step of the reaction, the primary amine of formula 9 is coupled with free carbocyclic acid of the cysteine derivative of formula 10, to form an amide group which produces a peptide linkage forming the compound of formula 11. The amino group of formula 9 is coupled with the free acid of the cysteine derivative 10, by any conventional peptide coupling method such as described above. In forming the compound of formula 11, $R_9$ of compound 10 can be any conventional amino protecting group utilized in peptide synthesis. Generally, preferred amino protecting groups are those which are cleavable under mildly acidic conditions of from about pH 2.0 to 3.0. Particularly, preferred amino protecting groups are tertiary lower alkoxy carbonyl group, for example the Boc group. Also in the compound of formula 10, $R_{10}$, is a thio protecting group. As described hereinabove, any suitable thio protecting group may be utilized.

Compound 10 at its asymmetric carbon atom denoted as "c" can have a specific stereoconfiguration. On the other hand compound 10 can be a mixture of stereoisomers. The stereoconfiguration of compound 10 is carried out throughout the entire reaction scheme. Therefore, the stereoconfiguration of the final product, compound 1 depends on the stereoconfiguration of compound 10. That is, at the asymmetric carbon atom denoted as "c", Compound 1 will have the same specific stereoconfiguration of compound 10, or if compound 10 is a mixture of stereoisomers then compound 1 will be a mixture of stereoisomers.

The amide coupling of the compounds of formulas 9 and 10 can be performed wherein both or either of compounds 9 and 10 have specific stereoconfigurations or mixtures thereof. Preferably, both compounds are derived from L-cysteine. Where mixtures of stereoisomers are used, compound 11 is produced as a mixture of stereoisomers that are maintained throughout the reaction scheme. Alternatively, where compound 11 is formed as one stereoisomer, the specific stereoconfiguration of that stereoisomer is maintained throughout the reaction scheme.

The compound of formula 11 is cyclized to form the compound of formula 12. Generally, cyclization of compound 11 can be effected by treatment in dilute solution of from 0.5–2 g/liter with a dichloromethane soluton of iodine at about room temperature giving the cyclic disulfide of formula 12. Under these conditions the thio protecting groups $R_{10}$ and $R_{10'}$ are removed from the compound of formula 11 to allow coupling of the two thio groups to cyclize the compound of formula 11 forming the cyclic disulide 12.

In the next step of the reaction, the compound of formula 13 is formed by selective removal of the $R_9$ amino protecting group from the compound of the cyclic disulfide 12. The cyclic disulfide 12 contains an amino protecting group $R_9$ and an ester protecting group $R_1$. Therefore, the compound of formula 12 should be treated under acidic conditions at low temperatures, preferably, 0–20° C., in 1 N HCl in ethyl acetate to remove the $R_9$ amino protecting group while leaving unaffected the $R_1$ ester protecting group to provide the free amine derivative 13 which is suitable for the next coupling step. In favorable cases, the product 13 may precipitate from the reaction mixture, in other cases, isolation can be effected by precipitation by the addition of a solvent such as ether or hexane or by careful concentration.

The specific stereoconfigurations of the asymmetric carbon atoms "c" and "d" in compound 11 are carried through to compound 13. Therefore, the stereoconfiguration(s) of compound 13 depend on the stereoconfigurations of compounds 7 and 10 used to produce compound 11.

The compound 19 can be prepared according to the procedure shown in Reaction Scheme 2 below.

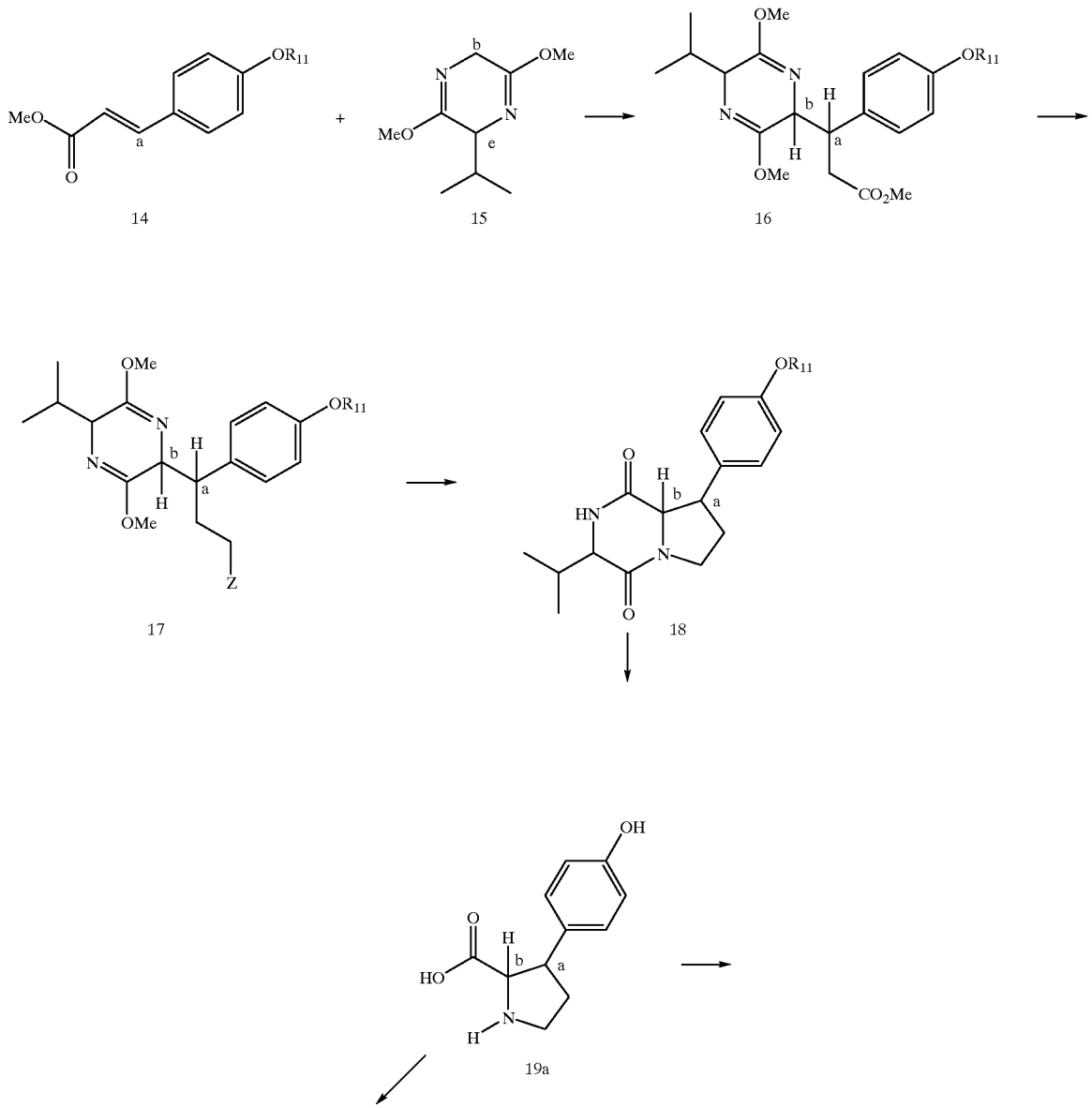

13

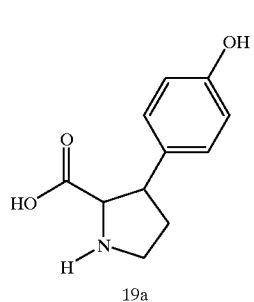

19a

-continued

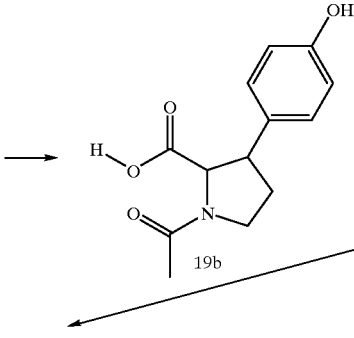

19b

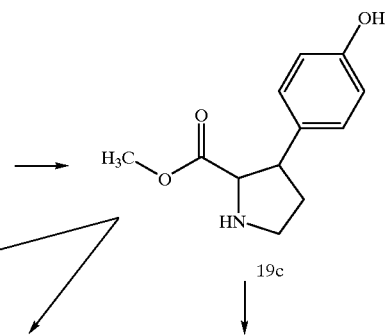

19c

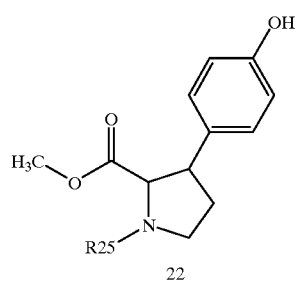

22

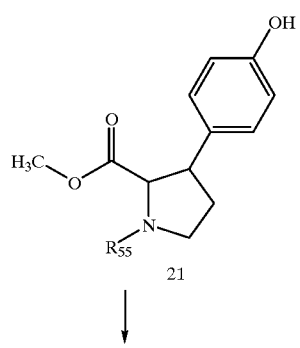

21

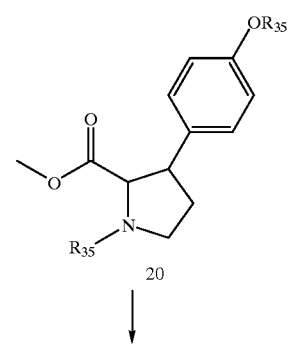

20

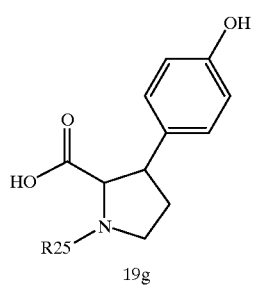

19g

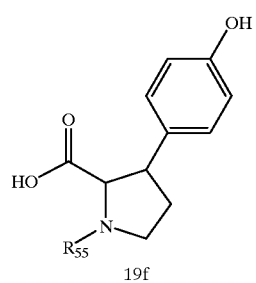

19f

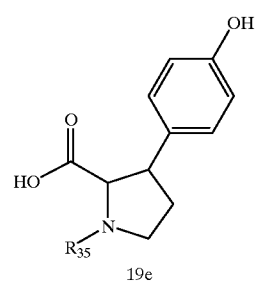

19e wherein $R_{11}$ is an ether protecting group; Z is a leaving group; $R_{25}$ is lower alkyl; $R_{35}$ is R—$SO_2$—; $R_{55}$ is $R_6$—$(CH_2)_m$—CO— or $R_8$—X—$(CH_2)_y$—CO—; R8—X—(CH2)y—CO—; R, $R_6$, $R_8$, X, y and m are as above.

The compound of formula 19 is produced by first reacting the compound of formula 14 with the compound of formula 15 to form the compound of formula 16. In accordance with this reaction, the compound 15 is added across the double bond of the compound of formula 14 by 1,4 enolate addition. Any conventional method of enolate addition across a double bond can be utilized in carrying out this reaction. For example, in carrying out this 1,4 enolate addition, compound 14 is converted into its lithium enolate by conventional means such as by reaction of the compound of formula 14 with the R-bislactime dimethyl ether of compound 15 and n-BuLi. Carrying out the reaction of compounds 14 and 15 at −60 to −78° C. gives the desired product 16.

At the asymmetric carbon atom denoted as "a", Compound 14 can exist as one of two possible geometric isomers or a mixture of those two geometric isomers. Likewise, because of the asymmetric carbon atom denoted as "e", compound 15 can exist as one specific stereoisomer or a mixture of steroisomers. Therefore, depending upon the specific stereoconfigurations of compounds 14 and 15, one of four possible stereoisomers of compound 16 or mixtures thereof can be produced. These various stereoconfigurations are carried through into compound 18.

The preferred stereoconfiguration of compound 16 is the following:

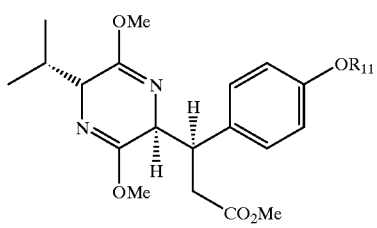

16'

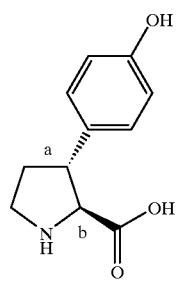

19I wherein $R_{11}$ is as above.

In the compound of formula 16, the $R_{11}$ group is preferably methyl. The compound of formula 16 is converted to the compound of formula 17 via reduction of the carboxymethyl group of the compound 16 to the corresponding $CH_2OH$ group and then converting the OH on the $CH_2OH$ group to a leaving group Z. Generally, this reduction reaction is carried out using a lithium aluminum or lithium borohydride reducing reagent, such as LiBH4 or LAH in a suitable inert solvent, for example THF, at a temperature of between −20° C. and room temperature, to provide a compound which is not normally isolated, but converted directly to compound 17 by reaction with a suitable agent to produce the leaving group Z which can be any conventional leaving group such as mesyloxy or tosyloxy. Any conventional means for reacting the compound 17 to produce the leaving group Z can be utilized, for example, treatment with methane sufonyl chloride in dichoromethane in the presence of tertiary amine base, for example, diisopropylethylamine.

The compound 17 is converted to the lactam 18 by cyclization in the presence of sodium iodide in DMF at a temperature of 60 to 130° C. Generally, the reaction isconveniently carried out by distilling off the lower boiling dichloromethane solvent as the reaction temperature rises to where the reaction is completed. The the lactam 18 can be isolated by conventional means such as silica gel chromatography. In forming lactam 18, the two methoxyl groups attached to carbons in the heterocyclic nitrogen containing ring of compound 17 are converted to carbonyl groups.

The lactam 18 is converted to the compound of formula 19a by hydrolysis. Any known method which will hydrolyze both the lactam group and the protecting group formed by $R_{11}$ in the compound of formula 18 can be used. For example, treatment of lactam 18 with 48% HBr in acetic acid at a temperature of 100 to 130° C. for several hours effects removal of the $R_{11}$ group and opens the lactam ring to provide 19a. Upon hydrolysis, the specific stereoconfigurations of the asymmetric carbon atoms "a" and "b" in compound 18 are carried through to compound 19a. Therefore, the stereo-configuration(s) of compound 19a will result from the stereoconfigurations of compounds 14 and 15 used to produce compound 16. The preferred stereoisomer of compound 19 is the following:

In accordance with this invention, the compound of formula 19a is converted to the compound of formula 19b by reacting compound of formula 19a with acetyl chloride in the presence of a weak organic base such as sodium bicarbonate. In this manner, the free amino group in the compound of formula 19b is protected.

The compound of formula 19b can be converted to the compound of formula 19c by treatment of the compound of formula 19c with anhydrous hydrochloric acid in methanol at a temperature of from 40° C. to 80° C. In this manner, the compound of formula 19b is converted to the protected acid of 19c now having a free amino group. The free amino group can be converted separately into the substituents $R_{25}$, $R_{55}$ and $R_{35}$.

In converting compound of formula 19c into the compound of formula 22 where $R_{25}$ is an alkyl group, the compound of formula 19c is treated reacted lower alkyl aldehyde form an intermediate amine which in turn is treated with a suitable, reducing agent such as sodium cyano borohydride typically in the presence of a weak organic acid, for example, acetic acid, to give the compound of formula 22. The compound of formula 22 is converted to the compound of formula 19g by hydrolysis under basic conditions such as treatment with an alkali base, for example, sodium hydroxide.

On the other hand, the compound of formula 19c can be converted to the compound of formula 19e by reaction with a lower alkyl sulfonyl chloride. In this manner, formula 19c is converted to the compound of formula 20. Any conventional method condensing a secondary amine with a lower alkyl sulfonyl chloride can be utilized in converting the compound of formula 19c to the compound of formula 20. The compound of formula 20 is converted to the compound of formula 19e by hydrolysis under basic conditions such as with an alkaline base, for example, sodium hydroxide under aqueous conditions. In this manner, one can produce the compound of formula 19e, where $R_{35}$ is a lower alkyl sulfonyl group.

The compound of formula 19c is converted to the compound of formula 21 by reacting the compound of formula 19 with an acylating agent, particularly reactive derivative of

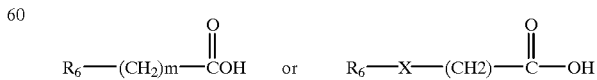

Reactive derivatives include acid halides or acid anhydrides. Any conventional method of acylating a secondary amine with these acid anyhydrides or acid halides can be used in this procedure. In this manner, one produces the compound of formula 19f.

The compound of formula 19 consists of the compounds of formula 19f, 19g and 19e. This compound can be converted to the compound of formula Ig by the following reaction scheme 3.

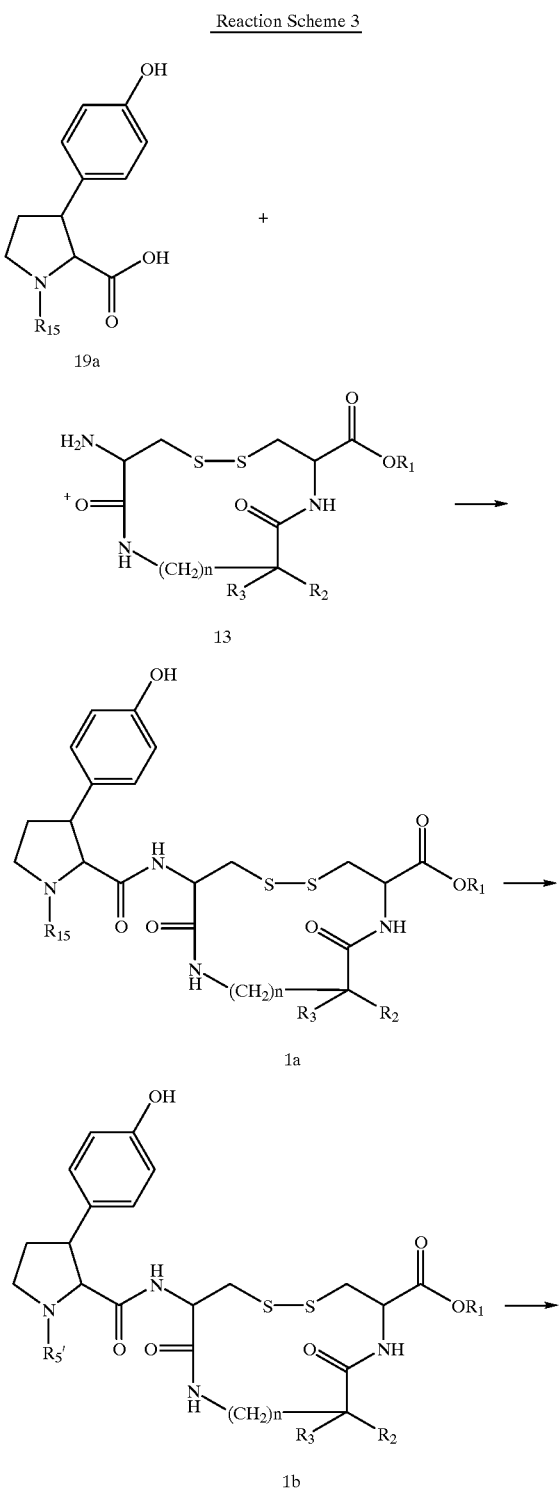

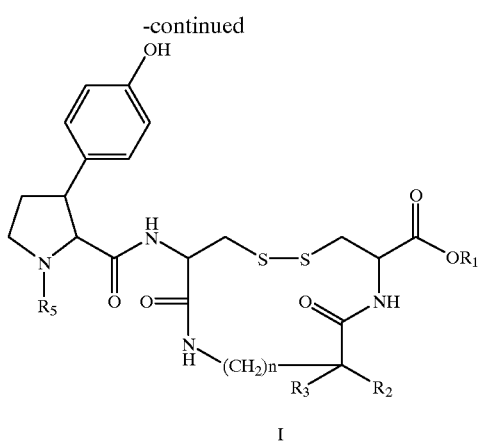

wherein $R_1$, $R_2$, $R_3$, $R_4$, $R_5$, $R_6$ and $R_{15}$ are as above.

As described above, the compounds of formulas 13 and 19 are converted to the compound of formula 1a by standard amide synthesis, for example by treatment of 13 and 19 with a slight excess of HBTU and diisopropylethylamine in an aprotic polar solvent such as DMF at a temperature of between room temperature and +45° C. to give a compound of formula 1a. $R_1$ with its attached oxygen atom forms a hydrolyzable ester group as described above. Further treatment of 1a under acidic conditions suitable for the cleavage of hydrolyzable esters, for example with 4N hydrochloric acid in dioxane/dichloromethane at room temperature and after completion of the reaction, precipitation of the product with ether produces the compound of the invention I.

In converting the compound of formula 1 a to the compound of formula 1 where $R_{15}$ is a tert. butoxy carbonyl group (Boc group) that is where $R_{15}$ is $R_8$—X—(CH2)y—CO—; and $R_8$ is tert. butyl, X is 0 and Y is zero, this group will be removed by acid hydrolysis from the compound of formula Ia to produce the compound of formula 1, $R_5$ is hydrogen. On the other hand, the compound of formula 1 where $R_5$ is hydrogen can be converted back to the Boc group by reacting the compound of formula 1 where $R_5$ is hydrogen with Boc anhydride under the same conditions utilized to form the compound of formula 21 from the compound of formula 19c. If the compound of formula 19g utilized as the starting material in reaction scheme 3 in place of the compound of 19a, the compound of formula 1 will be formed with the amino group being substituted with $R_{25}$. On the other hand if the compound of formula 19f is utilized in place of the compound of formula 19a, the reaction scheme 3, the compound of formula 1 will be formed with the substituent $R_{55}$. On the other hand, if the compound of formula 19e substituted for the compound of formula 19a in the reaction scheme 3. The compound of formula 1 will be formed with the substituent $R_{35}$.

The invention is further illustrated by the following examples. Terms used in the examples are defined as follows:

THF is tetrahydrofuran,
DMF is N,N-dimethylformamide,
HOBT is 1-hydroxybenzotriazole,
BOP is [(benzotriazole-1-yl)oxy]tris-(dimethylamino) phosphonium hexafluorophosphate,
HATU is O-(7-azabenzotriazol-1-yl)-1,1,3,3-tetramethyluronium hexafluorophosphate
HBTU is O-benzotriazole-N,N,N',N',-tetramethyluronium hexafluorophosphate,
DIPEA is diisopropylethylamine, DMAP is 4-(N,N-dimethylamino)pyridine
DPPA is diphenylphosphoryl azide
DBU is 1,8-diazabicyclo[5.4.0]undec-7-ene
NaH is sodium hydride
brine is saturated aqueous sodium chloride solution
TLC is thin layer chromatography
LiOH is lithium hydroxide
LDA is lithium diisopropylamide
BOP-Ci is bis(2-oxo-3-oxazolidinyl)phosphinic chloride
NMP is N-methyl pyrrolidinone
Fmoc is (9-fluorenylmethox)carbonyl
TFA is trifluoroacetic acid
HOAc is acetic acid
HRMS is high resolution mass spectroscopy
Trityl is triphenylmethyl
LAH is lithium aluminum hydride
DCM is dichloromethane
Boc is [[(1,1-dimetlhyl)ethoxy]carbonyl]-
Boc anhydride is di-tert-butyl-dicarbonate
Boc$_2$O is di-tert-butyl-dicarbonate
HRP is horseradish peroxidase
DMSO is dimethyl sulfoxide
BSA is bovine serum albumin
CHO is Chinese hamster ovary
EDTA is ethylenediamine tetraacetic acid
PMSF is ρ-toluenesulfonyl fluoride
PBS is phosphate buffer solution

EXAMPLE 1

Preparation of 1-(2-Azidoethyl)cyclopentane Carboxylic Acid

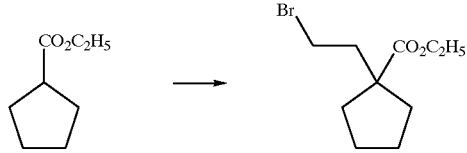

a. To an ice cold solution of diisopropylamine (56 mL, 0.396 mol) in THF 85 (mL) was added n-butyl lithium in hexane solution (240 mL, 1.6 M, 0.393 mol) over 20 min. The mixture was stirred at 0° C. for 30 min cooled to a bath temperature of −65° C. and ethyl cyclopentane carboxylate (37.4 g, 0.263 mol) in THF (50 mL) was added over 20 min. After 1 hour, a solution of 1,2-dibromoethane (47 mL, 0.545 mol) in THF (50 mL) was added, the mixture was held at −65° C. for 3 hour and allowed to warm to room temperature overnight. The reaction was quenched by addition of saturated ammonium chloride solution (200 mL), the layers were separated and the aqueous layer was extracted with ethyl acetate (100 mL). The combined extracts were washed with 1:1 brine:water (250 mL) and were dried (Na$_2$SO$_4$). The solution was filtered and concentrated, diluted with toluene (100 mL) and concentrated. The dilution and concentration was repeated twice to give the bromide which is ethyl 1-(2-bromoethyl)cyclopentane carboxylate (52.5 g).

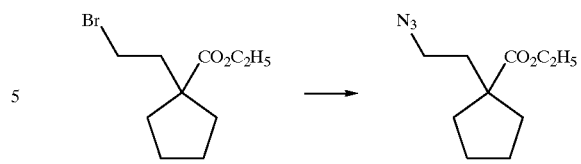

b. A solution of the above bromide (52.5 g, 0.211 mol) and sodium azide (54 g, 0.831 mol) in DMF (200 mL) was stirred at 50° C. for 5 hour under a nitrogen atmosphere and was filtered. The filtrate was concentrated to near dryness, diluted with ethyl acetate (500 mL), filtered and concentrated to give crude ethyl 1-(2-azidoethyl)cyclopentane carboxylate (40.9 g) as a brown oil. This material was combined with product from a previous run (total 63.5 g) and was purified by chromatography over 250 g of silica gel, eluting with 5% ethyl acetate in hexane to give 50.3 g of ethyl 1-(2-bromoethyl)cyclopentane carboxylate as a light brown oil.

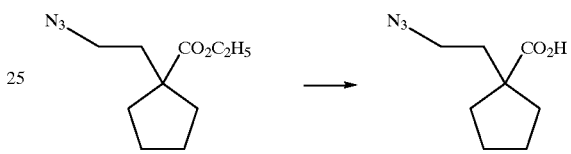

c. The ethyl 1-(2-bromoethyl)cyclopentane carboxylate from above (50.3 g, 0.238 mol) was dissolved in THF (750 mL) and methanol (375 mL) and a solution of Lithium hydroxide hydrate (15 g, 0.357 mol) in water (300 mL) was added. The resulting solution was stirred at 40° C. overnight and concentrated. The residue was dissolved in 2 L of water containing 40 mL of 1N sodium hydroxide and was washed with hexane (1 L). The aqueous layer was acidified with 1 N HCl (375 mL) and was extracted with ether (2×1 L). The combined extracts were dried (Na$_2$SO$_4$) and concentrated to give 1-(2-azidoethyl)cyclopentane carboxylic acid (37.5 g) as an amber liquid.

EXAMPLE 2

Preparation of N-Fluorenylmethoxycarbonyl-S-trityl-L-Cysteine-t-butyl Ester

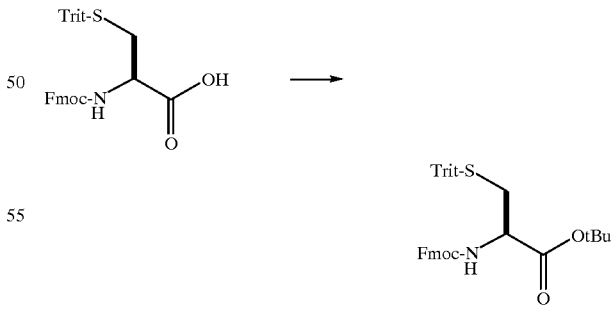

A suspension of Fmoc-S-trityl-L-cysteine (2.9 g, 5 mmol) in dry toluene (10 mL) was heated to 80° C. To this suspension was added over 20 min., di-tert-butyl-dimethylformamide acetal (4.8 mL, 20 mmol). The solution was cooled, washed with water, saturated sodium bicarbonate (2×10 mL), and evaporated. The residue was purified by flash chromatography eluting with ethyl acetate/hexanes (15/85), to give 2.2 g of N-Fluorenylmethoxycarbonyl-S-trityl-L-Cysteine-t-butyl ester.

EXAMPLE 3

Preparation of N-[[1-(2-Azidoethyl)cyclopentyl]carbonyl]-S-triphenylmethyl-L-cysteine 1,1-dimethylethyl Ester

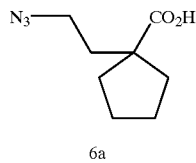

6a

+

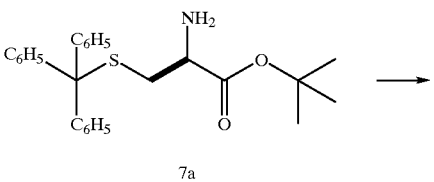

7a

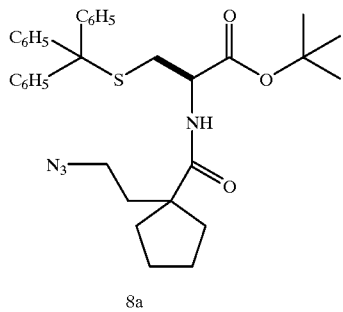

8a

To a solution of N-fluorenylmethoxycarbonyl-S-trityl-L-cysteine 1,1-dimethylethyl ester (640 mg, 1 mmol) in 5 mL of DMF was added 2 mL of piperidine. The solution was stirred for 20 min., and the solvent was evaporated. The residual piperidine was removed by azeotroping the solid with DMF (3×20 mL) and drying under high vacuum for 1 hour to give S-trityl-L-cysteine 1,1-dimethylethyl ester as a solid. To this solid was added 5 mL of DMF followed by 1-(2-azidoethyl)cyclopentane carboxylic acid (6a) (183 mg, 1 mmol), HBTU (379 mg, 1 mmol), and DIPEA (0.18 mL, 1 mmol). The resulting solution was stirred for 5 hours, and the solvent was removed under high vacuum. The residue was purified by silica gel column chromatography usilng ethylacetate/hexanes (15/85) as eluent, to afford 500 mg (86%) of N-[[1-(2-azidoethyl)cyclopentyl]carbonyl]-S-triphenylmethyl-L-cysteinie 1,1-dimethylethyl ester.

EXAMPLE 4

Preparation of 2(R)-[[[1-[[2(R)-[[(1,1-dimethylethoxy)carbonyl]amino]-1-oxo-3-[(triphenylmethyl)thio]propyl]amino]ethyl]cyclopentyl]carbonyl]amino-3-[(triphenylmethyl)thio]propanoic Acid 1,1-dimethylethyl Ester (11a)

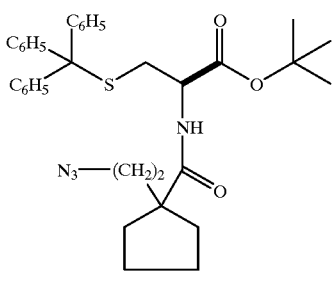

8a

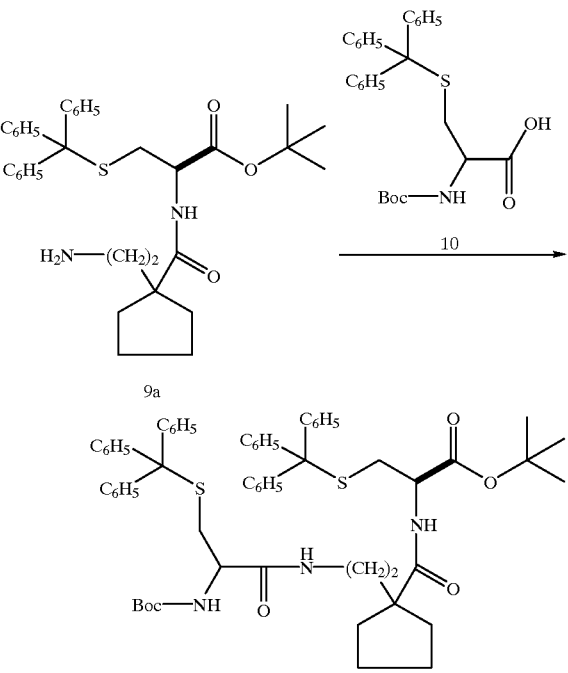

To a solution of N-[[1-(2-azidoethyl)cyclopentyl]carbonyl]-S-triphenylmethyl-L-cysteine 1,1-dimethylethyl ester (500 mg, 0.86 mmol) in 5 mL of THF, was added under argon, a solution of trimethylphosphine in THF (1.41 mL of 1 M solution, 1.5 equiv.). The solution was stirred for 3 hours, after which 6 drops of water were added. The resulting solution was stirred for 15 minutes, the solvent was evaporated under vacuum, and the residue dried under high vacuum for 14 hours. To the resulting oil was added a solution of N-[(1,1-dimethylethoxy)carbonyl]-S-trityl-L-cysteine 10 (463 mg, 1 mmol), HBTU (379 mg, 1 mmol), and DIPEA (0.18 mL, 1 mmol) in 5 mL of DMF. The solution was stirred for 6 hours, and the solvent was evaporated under high vacuum. The residue was purified by silica gel chromatography eluting with 35% ethyl acetate in hexane, to yield 510 mg of 2(R)-[[[1-[[2(R)-[[(1,1-dimethylethoxy)carbonyl]amino]-1-oxo-3-[(triphenylmethyl)thio]propyl]amino]ethyl]cyclopentyl]carbonyl]amino-3-[(triphenylmethyl)thio]propanoic acid 1,1-dimethylethyl ester (11a) (59%).

EXAMPLE 5

Preparation of (8R,13R)-13-[[(1,1-dimethylethoxy)carbonyl]amino]-6,14-dioxo-10,11-dithia-7,15-diazaspiro[4.12]heptadecane-8-carboxylic Acid 1,1-dimethylethyl Ester

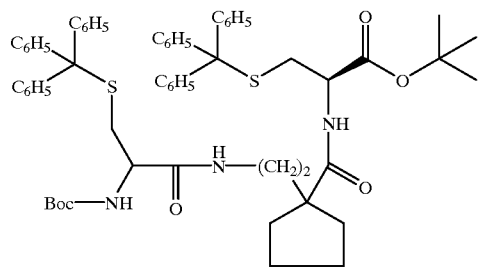

11a

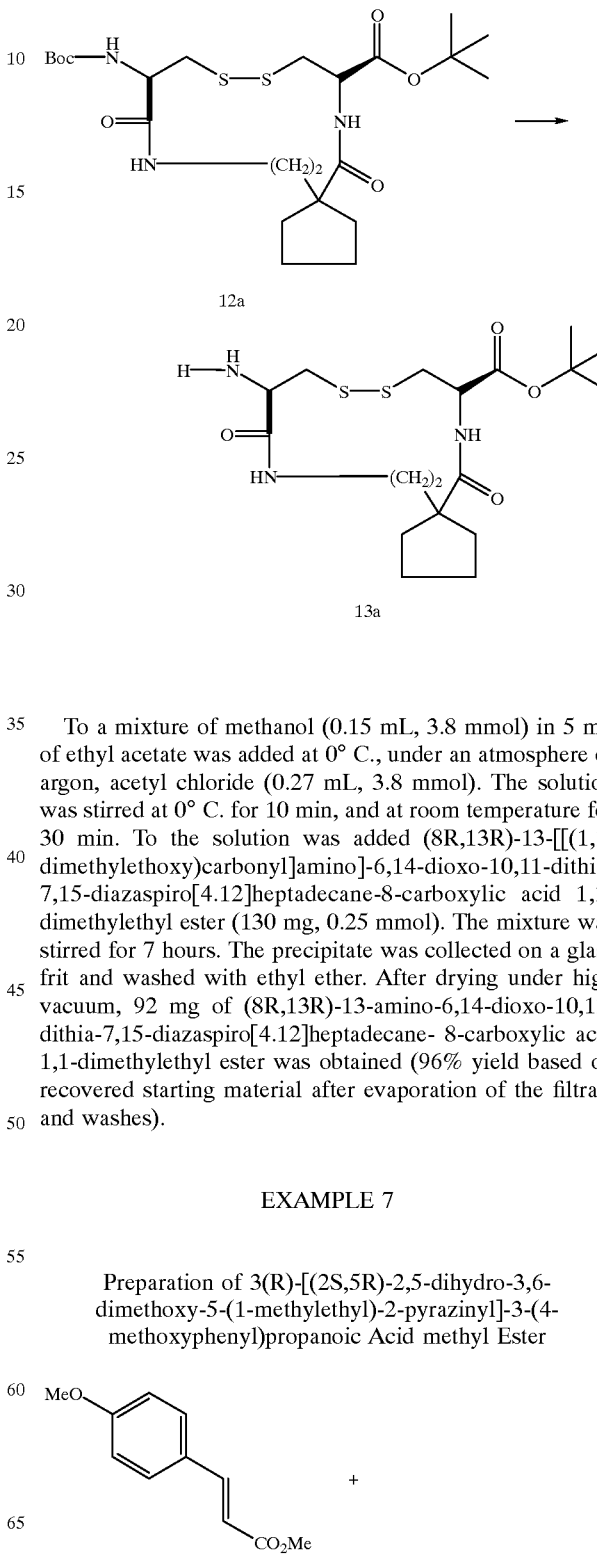

12a

To a solution of 2(R)-[[[1-[[2(R)-[[(1,1-dimethylethoxy)carbonyl]amino]-1-oxo-3-(triphenylmethyl)thio]propyl]amino]ethyl]cyclopentyl]carbonyl]amino-3-[(triphenylmethyl)thio]propanoic acid 1,1-dimethylethyl ester (11a) (510 mg, 0.51 mmol) in 500 mL of 9/1 dichloromethane-methanol was added over 5 min., a solution of iodine (520 mg, 4 equiv.) in 500 mL of 9/1 dichloromethane-methanol. The resulting reaction mixture was stirred for 10 min., and was quenched with 300 mL of 0.1 M $Na_2S_2O_3$. The layers were separated, and the aqueous layer was extracted with 200 mL of dichloromethane. The combined organic layers were washed with water, dried over magnesium sulfate, and evaporated to give an oil. Purification by silica gel chromatography eluting with 1/1 ethyl acetate/hexane afforded 160 mg (61%) of (8R,13R)-13-[[(1,1-dimethylethoxy)carbonyl]amino]-6,14-dioxo-10,11-dithia-7,15-diazaspiro[4.12]heptadecane-8-carboxylic acid 1,1-dimethylethyl ester.

EXAMPLE 6

Preparation of (8R,13R)-13-amino-6,14-dioxo-10,11-dithia-7,15-diazaspiro[4.12]heptadecane-8-carboxylic Acid 1,1-dimethylethyl Ester

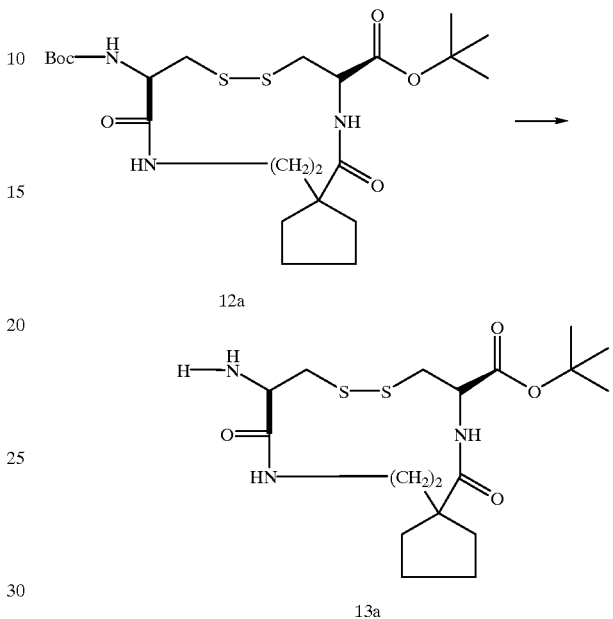

12a

13a

To a mixture of methanol (0.15 mL, 3.8 mmol) in 5 mL of ethyl acetate was added at 0° C., under an atmosphere of argon, acetyl chloride (0.27 mL, 3.8 mmol). The solution was stirred at 0° C. for 10 min, and at room temperature for 30 min. To the solution was added (8R,13R)-13-[[(1,1-dimethylethoxy)carbonyl]amino]-6,14-dioxo-10,11-dithia-7,15-diazaspiro[4.12]heptadecane-8-carboxylic acid 1,1-dimethylethyl ester (130 mg, 0.25 mmol). The mixture was stirred for 7 hours. The precipitate was collected on a glass frit and washed with ethyl ether. After drying under high vacuum, 92 mg of (8R,13R)-13-amino-6,14-dioxo-10,11-dithia-7,15-diazaspiro[4.12]heptadecane- 8-carboxylic acid 1,1-dimethylethyl ester was obtained (96% yield based on recovered starting material after evaporation of the filtrate and washes).

EXAMPLE 7

Preparation of 3(R)-[(2S,5R)-2,5-dihydro-3,6-dimethoxy-5-(1-methylethyl)-2-pyrazinyl]-3-(4-methoxyphenyl)propanoic Acid methyl Ester

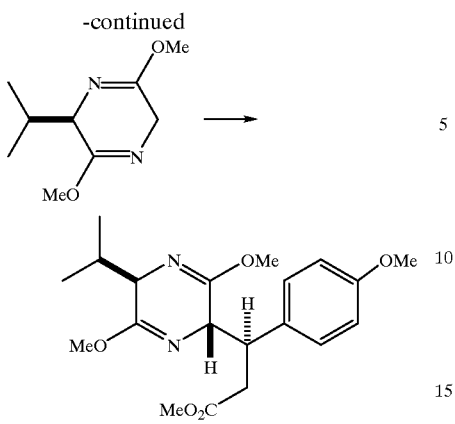

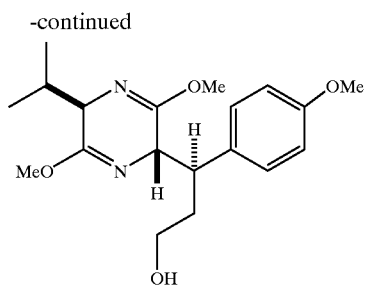

To a solution of (R)-2,5-dimethoxy-3-isopropyl-3,6-dihydropyrazine (18.4 g, 100 mmol) in 250 mL of dry THF at −70° C. (internal temperature) was added dropwise a solution of n-BuLi (1.6 M in hexane, 63 mL, 100 mmol) over 3 hours so as to maintain the internal temperature below −70° C. After addition, the solution was stirred at −70° C. for 40 min. To the solution was then added 90 mL of a THF solution of methyl trans-4-methoxycinnamate (21.2 g, 110 mmol) over 1 hour. The resulting solution was stirred at −70° C. for additional 4 hours. The reaction was quenched by the addition of acetic acid (6.1 mL, 100 mmol) at −70° C. and the resulting suspension was warmed to room temperature to give a yellow solution. The solution was diluted with ether to 1000 mL and the organic layer was washed with water (3×80 mL) and brine (3×80 mL) and dried over $MgSO_4$. After removal of the solvent, the residue (44.3 g) was purified by HPLC on silica gel, eluting with ethyl acetate/hexane (1:5.5) to give 3(R)-[(2S,5R)-2,5-dihydro-3,6-dimethoxy-5-(1-methylethyl)-2-pyrazinyl]-3-(4-methoxyphenyl)propanoic acid methyl ester (30.6 g, 81.3 mmol, 81.3%). TLC: Rf=0.3, ethyl acetate/hexane (1/5). HRMS, obs. 377.2071, calc. 377.2076. Anal. cacld for $C_{20}H_{26}N_2O_5$: C, 64.16; H, 7.00; N, 7.48. Found: C, 64.05; H, 7.28; N, 7.37.

EXAMPLE 8

Preparation of 3(R)-1(2S,5R)-2,5-dihydro-3,6-dimethoxy-5-(1-methylethyl)-2-pyrazinyl]-3-(4-methoxyphenyl)propano]

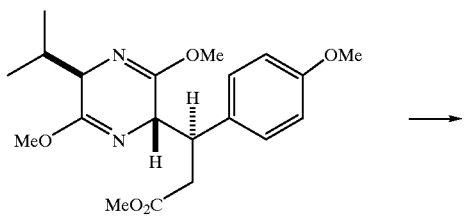

In a dry two-necked flask equipped with dropping funnel and thermometer was added 3(R)-[(2S,5R)-2,5-dihydro-3,6-dimethoxy-5-(1-methylethyl)-2-pyrazinyl]-3-(4-methoxyphenyl)propanoic acid methyl ester (17.5 g, 46.48 mmol) and 559 mL of dry THF. The solution was then cooled to −10° C. in an acetone-ice bath under argon. To the solution was added dropwise a solution of lithium aluminum hydride in THF (0.8 M, 60 mL, 48 mmol) at a rate so as to maintain the internal temperature below 0° C. After the addition, the ice bath was removed, and reaction mixture was stirred at room temperature for 2 hours. The reaction was quenched by the addition of 10 mL of ethyl acetate followed by 25 mL of saturated sodium sulfate solution. The resulting white precipitate was filtered and was washed with ethyl acetate (4×100 mL). The combined filtrate was then concentrated to give 3(R)-[(2S,5R)-2,5-dihydro-3,6-dimethoxy-5-(1-methylethyl)-2-pyrazinyl]-3-(4-methoxyphenyl)propanol, as a colorless oil (17.7 g). TLC (Rf: 0.5, ethyl acetate/hexane=1:1) single spot.

EXAMPLE 9

Preparation of methanesulfonic Acid 3(R)-[(2S,5R)-2,5-dihydro-3,6-dimethoxy-5-(1-methylethyl)-2-pyrazinyl]-3-(4-methoxyphenyl)propyl Ester (29)

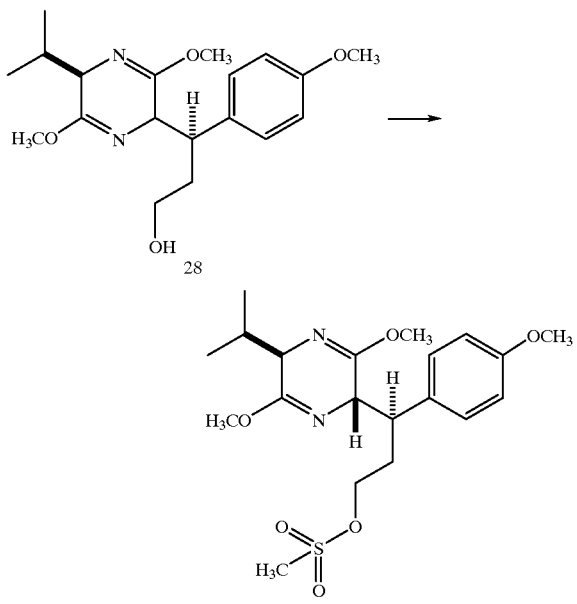

The above oil 3(R)-[(2S,5R)-2,5-dihydro-3,6-dimethoxy-5-(1-methylethyl)-2-pyrazinyl]-3-(4-methoxyphenyl)propanol (28) (17.7 g) was dissolved in 300 mL of dichloromethane. To the solution at –5° C. was added methane sulfonyl chloride (8.02 g, 5.42 mL, 70 mmol) followed by diisopropylethylamine (DIPEA, 12 mL, 70 mmol) dropwise over 10 min. The reaction was stirred at 0° C. for 2 hour. The light yellow solution was diluted with 2 L of ether and was washed with water (3×200 mL) and brine (2×200 mL). After it was dried over sodium sulfate, the solution was concentrated to a volume of 160 mL under vacuum at 20° C. TLC in EA/H (=1:1): Rf=0.74, as a major spot; Rf=0.21, as a minor spot.

EXAMPLE 10

Preparation of (3R,8R,8aS)-hexahydro-8-(4-methoxyphenyl)-3-(1-methylethyl)pyrrolo[1,2-a]pyrazine-1,4-dioxide (30)

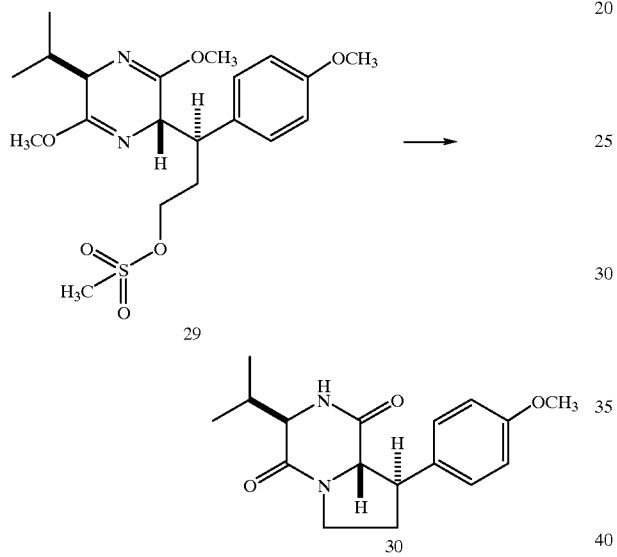

To a 2L, three-necked flask equipped with a pressure equalized dropping funnel, a thermometer and a short path still head was charged with 1,000 mL of DMF and sodium iodide (33 g, 200 mmol). The solution of the crude methane sulfonate 29, obtained above in Example 9, was added to the DMF solution through the dropping funnel over 1.2 hour at a bath temperature of 60–120° C. under argon. After the addition, the low boiling components were removed by distillation via the still head at 100 mm pressure. The residue was stirred at 120° C. (internal temperature) for an additional 2.5 hours. After the reaction mixture was cooled to room temperature, the solvent was evaporated under vacuum and the residue was diluted with ethyl acetate (700 mL). The resulting white solid was collected by filtration, washed with ethyl acetate (3×100 mL) and discarded. The combined filtrate was washed with water (3×100 mL). The water layer was saturated with NaCl and extracted with ethyl acetate (3×200 mL). The combined ethyl acetate layers were dried over sodiun sulfate and concentrated to give 16.5 g of crude 30. After filtration through 300 g of silica gel eluting with ethyl acetate, 30 was obtained (11.5 g containing 1 equivalent of DMF). HPLC purification on a silica gel column eluting with ethyl acetate:hexane (8:1) yielded 9.3 g of 30 as a white foamy solid, HRMS (M+H): obs. 302.1627, calcd. 302.1630.

EXAMPLE 11

Preparation of (+)-(2S,3R)-1-acetyl-3-(4-hydroxy)phenylproline (29)

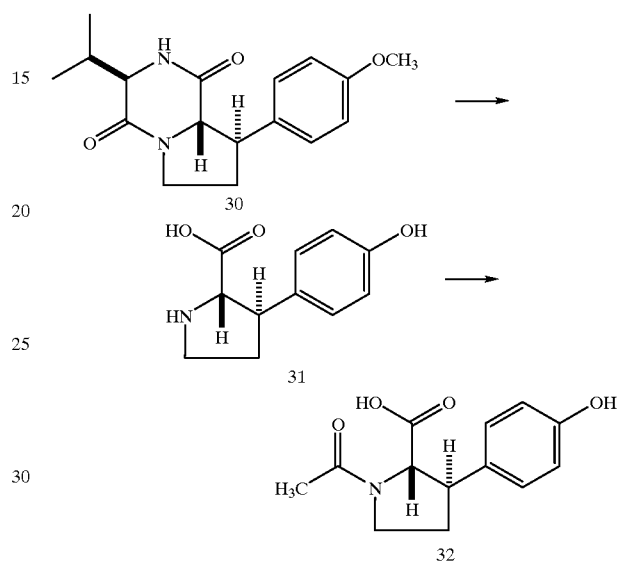

The compound 30 obtained above in example 10 (8.0 g, 26.45 mmol) was dissolved in 60 mL of 48% aqueous hydrobromic acid and 18 mL of acetic acid. The solution was stirred at a bath temperature of 130–135° C. for 3.5 hours. The reaction was monitored by reverse-phase HPLC. A total of 65 mL of solvent was then distilled under vacuum and the residue was cooled to room temperature. The resulting white crystalline solid (valine hydrobromide, 2.15 g) was removed by filtration and the filtrate was diluted with water (70 mL). The aqueous layer was treated with solid NaHCO$_3$ (25.6 g) to give a brown suspension of 31. To the above suspension was then added acetyl chloride (12.2 mL, 171 mmol) in 60 mL of THF over 2 hour at 20° C. During the addition, another 1.2 g of NaHCO$_3$ was added in several portions to maintain the reaction pH above 7. After addition the suspension was stirred at room temperature overnight. After acidification with TFA to pH<3, the suspension was concentrated to dryness and the brown residue was extracted with acetone (2×250 mL). The acetone solution was dried over sodium sulfate and concentrated to give a brown gum. This brown residue was extracted with hot ethyl acetate (2×250 mL) to remove N-acetylvaline. The remaining brown gum (11.2 g) was dissolved in 60 mL of water and purified by RP-HPLC (5×30 cm Waters C-18 Delta Prep column eluting with a linear gradient of 5% to 95% acetonitrile in water, 150 mL/min) to give (+)-(2S,3R)-1-methylcarbonyl-3-(4-hydroxy)phenylproline (32) as a white solid (3.45 g, 14.24 mmol) (53.8%). HRMS (M+H), obs. 250.1078, calcd. 250.1079.

EXAMPLE 12

Preparation of (8R,13R)-13-[[[1-acetyl-3-(R)-(4-hydroxyphenyl)-2-(S)-pyrrolidinyl]carbonyl]amino]-6,14-dioxo-10,11-dithia-7,15-diazaspiro[4.12]heptadecane-8-carboxylic Acid

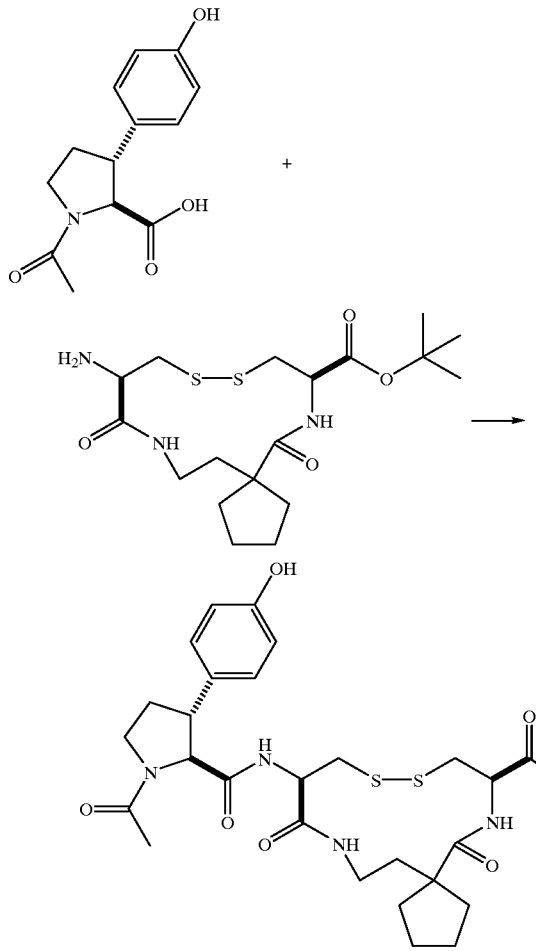

To a solution of (2S,3R)-1-methylcarbonyl-3-(4-hydroxy)phenylproline (29), prepared in Example 11, (1.37 g, 5.5 mmol) and (8R,13R)-13-amino-6,14-dioxo-10,11-dithia-7,15-diazaspiro[4.12]heptadecane-8-carboxylic acid 1,1-dimethylethyl ester prepared in example 6, (2.27 g, 5.0 mmol) in 20 mL of DMF was added HBTU (2.08 g, 5.5 mmol) and DIPEA (2.7 mL, 15 mmol) at room temperature. The solution was stirred under argon for 1.5 hours. The reaction was then quenched with 30 mL of brine and the resulting mixture was extracted with ethyl acetate (3×100 mL). The combined organic layers were washed with 0.1 N hydrogen chloride, sat. NaHCO$_3$, and brine (2×30 mL, each) and were dried over Na$_2$SO$_4$. After removal of solvent, the resulting yellow foam was recrystallized from dichloromethane-hexane to give (8R,13R)-13-[[[1-acetyl-3-(R)-(4-hydroxyphenyl)-2-(S)-pyrrolidinyl]carbonyl]amino]-6,14-dioxo-10,11-dithia-7,15-diazaspiro[4.12]heptadecane-8-carboxylic acid 1,1-dimethylethyl ester as a light yellow powder (3.01 g).

To a solution of this ester (3.01 g) in 15 mL of dry dichloromethane was added 4N HCl in dioxane (50 mL) in one portion at room temperature. The resulting solution was stirred at room temperature for 4.5 hours to give a suspension. The suspension was diluted with 50 mL of mixed solvent (3:7 dichloromethane:ether) and was filtered. The light yellow filter-cake was washed with above mixed solvent (2×20 mL) followed by ether (2×20 mL). The cake was dried under vacuum to give a light yellow powder (2.51 g, HLPC purity: >85%). The final purification was effected with RP-HPLC to give (8R,13R)-13-amino-6,14-dioxo-10,11-dithia-7,15-diazaspiro[4.12]heptadecane-8-carboxylic acid as a white solid (1.55 g, 2.61 mmol) in 52 % yield. HRMS (M+H) Obs. 593.209, Calcd. 593.2103.

EXAMPLE 13

Preparation of 1-(2-azidoethyl)cyclohexane carboxylic Acid

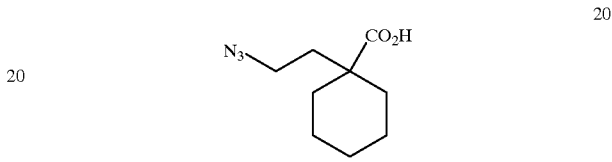

Using the method described in example 1 and starting with cyclohexane carboxylic acid ethyl ester, 1-(2-azidoethyl) cyclohexane carboxylic acid was obtained as an oil. Low resolution mass spectrum (ES-) m/z 196.1 [(M-H) Calcd for C$_9$H$_{14}$N$_3$O$_2$: 196.1].

EXAMPLE 14

Preparation of N-[[(1-(2-azidoethyl)cyclohexane9 carbonyl]-S-triphenylmethyl-L-cysteine methyl Ester (22)

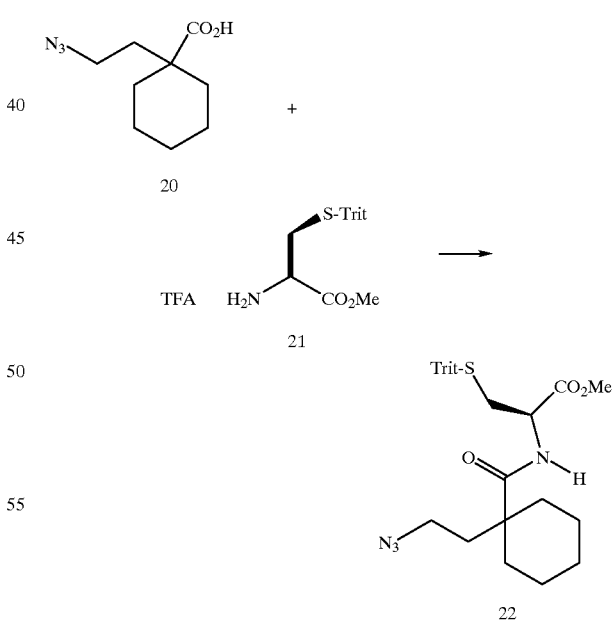

To a solution of 1-(2-azidoethyl)cyclohexane carboxylic acid (20) (0.60 g, 3.0 mmole), the TFA salt of S-triphenylmethyl-L-cysteine methyl ester (1.4 g, 3.0 mmole) and diisopropylethylamine (0.78 g, 6.0 mmole) in DMF (12 ml) was added HBTU (1.1 g, 3.0 mmole). The resultant mixture was stirred at room temperature for 4 hours. The reaction mixture was poured into a separatory funnel containing ethyl acetate (100 mL) and water (35 mL). The aqueous layer was separated and back extracted with ethyl acetate (2×50 mL. The combined organic layers were washed with sat. brine, dried over $MgSO_4$, filtered and concentrated in vacuo. Purification by flash column chromatography, eluting with hexane:ethyl acetate (8:1), afforded azide 22 (1.25 g, 74%) as a white solid. High resolution mass spectrum m/z 579.2396 [(M+Na)$^+$; Calcd for $C_{32}H_{36}N_4O_3SNa$: 579.2406].

EXAMPLE 15

Preparation of methyl ester 23 N-[[(1-1(2-[(1,1-dimethyethoxy)carbonyl]amino]-ethyl]cyclohexane]carbonyl]-S-triphenylmethyl-L-cysteine methyl Ester

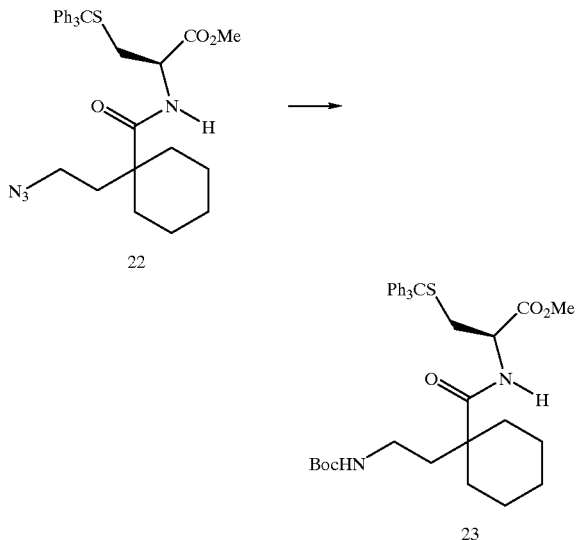

EXAMPLE 16

Preparation of 2(R)[[[1-[2-[[3-[[(acetylamino)methyl]thio]-2(R)-[[(9H-fluoren-9-ylmethoxy)carbonyl]amino]-1-oxopropyl]amino]ethyl]cyclohexyl]carbonyl]amino]-3-[(triphylmethyl)thio] propanoic Acid methyl Ester (24)

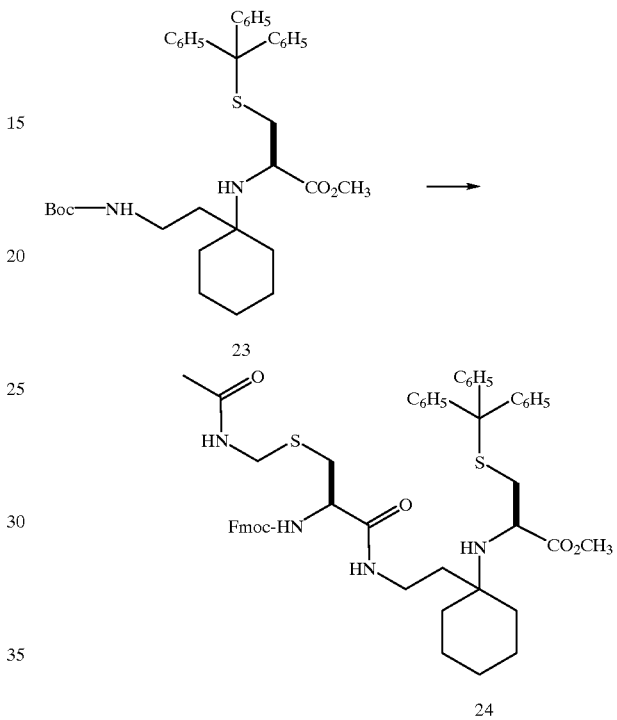

To a solution of the azide 22 obtained above in example 14 (1.24 g, 2.2 mmole) in THF (10 ml) was added trimethylphosphine (2.5 ml, 1M in THF, 2.5 mmole) dropwise. The resultant mixture was stirred at room temperature for 30 min. and water (0.080 g, 4.5 mmole) was added to the reaction mixture. After stirring for 2 h, the reaction mixture was diluted with $CH_2Cl_2$ (70 mL, dried over $Na_2SO_4$, filtered and concentrated in vacuo. The oil was dried under high vacuum for 5 h.

The crude amine was dissolved in ethyl acetate (10 mL) and $Boc_2O$ (1.0 g, 4.6 mmole) was added to the mixture. The resultant mixture was stirred overnight. The reaction mixture was poured into a separatory funnel containing ethyl acetate (75 mL) and water (25 mL). The aqueous layer was separated and back extracted with ethyl acetate (1×50 mL). The combined organic layer was washed with saturated brine, dried over $MgSO_4$, filtered and concentrated in vacuo. Purification by flash column chromatography, eluting with hexane-ethyl acetate (6:1 then 4:1), afforded N-[[(1-[(2-[[(1,1-dimethyethoxy)carbonyl]amino]ethyl]cyclohexane]carbonyl]-S-triplhenylmethyl-L-cysteine methyl ester (23) (0.88 g, 62%). High resolution mass spectrum m/z 653.3007 [(M+Na)$^+$; Calcd for $C_{37}H_{46}N_2O_5SNa$: 653.3025].

To a solution of the ester 23 (0.88 g, 1.4 mmole), produced in Example 15, in dichloromethane (10 ml) was added TFA (5 ml). The mixture was stirred for 45 min. and was concentrated in vacuo. The TFA salt was dried under high vacuum for 2 hours.

To a solution of the crude TFA salt, Fmoc-Cys(Acm)-OH (575 mg, 1.4 mmol) and diisopropylethylamine (1 ml, excess) in DMF (10 ml) was added HBTU (595 mg, 1.6 mmole). The resultant mixture was stirred overnight. The reaction mixture was poured into a separatory funnel containing ethyl acetate (150 ml) and washed with 0.3M HCl (2×30 ml). The aqueous layers were combined and back extracted with ethyl acetate (1×50 ml). The combined organic layer was washed with sat. $NaHCO_3$ (1×30 ml), dried over $MgSO_4$, filtered and concentrated in vacuo. Purification by flash column chromatography, eluting with hexane-ethyl acetate (1:1 then 2:3), afforded 2(R)[[[1-[2-[[3-[[(acetylamino)methyl]thio]-2(R)-[[(9H-fluoren-9-ylmethoxy)carbonyl]amino]-1-oxopropyl]amino]ethyl]cyclohexyl]carbonyl]amino]-3-[(triphylmethlyl)thio]propanoic acid methyl ester (24) (1.05 g, 80%). HRMS: ($C_{53}H_{58}N_4O_7S_2$): obs, m/z 949.3636 (M+Na)$^+$. Calcd 949.3645.

EXAMPLE 17

Preparation of 2(R)[[[1-[2-[[3-[[(acetylamino)methyl]thiol-2(R)-[[2(S)3(R)-1-acetyl-3-(4-hydroxyphenyl)pyrrolidin-2-yl]carbonyl]amino]-1-oxopropyl]amino]ethyl]-cyclohexyl]carbonyl]amino]-3-[(triphylmethyl)thio]propanoic Acid methyl Ester

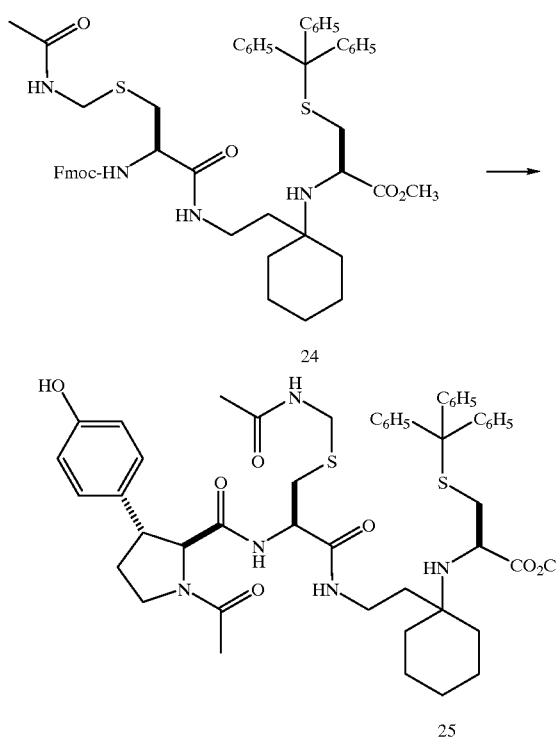

EXAMPLE 18

Preparation of 2(R)[[[1-[2-[[3-[[(acetylamino)methyl]thio-2(R)-[[2(S)3(R)-1-acetyl-3-(4-hydroxyphenyl)pyrrolidin-2-yl]carbonyl]amino]-1-oxopropyl]amino]ethyl]-cyclohexyl]carbonyl]amino]-3-1(triphylmethyl)thio]propanoic Acid (26)

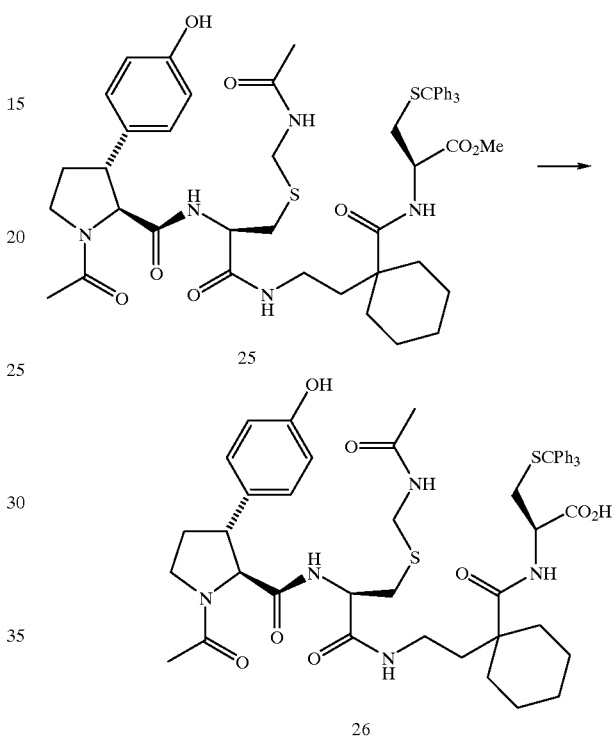

To a solution of compound 2(R)[[[1-[2-[[3-[[(acetylamino)methyl]thio]-2(R)-[[(9H-fluoren-9-ylmethoxy)carbonyl]amino]-1-oxopropyl]aminolethyl]cyclohexyl]-carbonyl]amino]-3-[(triphylmethyl)thio]propanoic acid methyl ester (24) (500 mg, 0.54 mmol) in DMF (3 ml) was added piperidine (2 ml). The mixture was stirred for 1 h and was concentrated under vacuum. The residue was dried at high vacuum overnight. The crude residue was washed with hexane (3×25 ml) and was dried under high vacuum for 45 min. to provide the crude amine (364 mg) resulting from removal of the Fmoc group from 24. This crude amine was stored under argon at −10° C.

To a solution of the above amine (50 mg, 0.07 mmol), (2S,3R)-1-acetyl-3-(4-hydroxy)phenylproline (32) (18 mg, 0.07 mmole) and diisopropylethylamine (0.05 ml, excess) in DMF (1 ml) was added HBTU (30 mg, 0.08 mmole). The resultant mixture was stirred at room temperature for 3.5 h. The reaction mixture was poured into a separatory funnel containing ethyl acetate (50 ml) and washed with 0.5M HCl (2×15 ml). The aqueous layers were combined and back extracted with ethyl acetate (1×20 ml). The combined organic layer was washed with sat. NaHCO$_3$ (1×15 ml), dried over MgSO$_4$, filtered and concentrated in vacuo to afford 50 mg of crude 25. This material was difficult to purify, therefore full characterization was carried out after hydrolysis of the methyl ester.

To a solution of 2(R)[[[1-[2-[[3-[[(acetylamino)methyl]thio]-2(R)-[[2(S)3(R)-1-acetyl-3-(4-hydroxyphenyl)pyrrolidin-2-yl]carbonyl]amino]-1-oxopropyl]amino]ethyl]-cyclohexyl]carbonyl]amino]-3-[(triphylmethyl)thio]propanoic acid methyl ester (25) (50 mg crude) in MeOH (0.5 ml) was added a solution of lithium hydroxide (2.5 mg, 0.060 mmol) in water (0.25 ml). The mixture was stirred for 2 h and the reaction mixture was made acidic (pH ~1–2) with 0.5M HCl (several drops). The reaction mixture was poured into a separatory funnel containing ethyl acetate (20 ml) and water (5 mL). The aqueous layer was separated and back extracted with ethyl acetate (2×10 mL). The combined organic layer was washed with saturated brine, dried over MgSO$_4$, filtered and concentrated under vacuum. Purification by reversed-phase HPLC, using a 15–95% acetonitrile-water gradient over 25 min., provided 2(R)[[[1-[2-[[3-[[(acetylamino)methyl]thio]-2(R)-[[2(S)3(R)-1-acetyl-3-(4-hydroxyphenyl)pyrrolidin-2-yl]carbonyl]amino]-1-oxopropyl]amino]ethyl]cyclohexyl]carbonyl]amino]-3-[(triphyinethyl)thio]propanoic acid (26) (42 mg). High resolution mass spectrum m/z 944.3701 (M+Na)$^+$; Calcd for C$_{50}$H$_{59}$N$_5$O$_8$S$_2$Na: 944.3703.

EXAMPLE 19

Synthesis of (9R,14R)-14-[[[1-acetyl-3-(R)-(4-hydroxyphenyl)-2-(S)-pyrrolidinyl]-arbonyl]amino]-7,15-dioxo-11,12-dithia-8,16-diazaspiro[5.12]Octadecane-9-carboxylic Acid

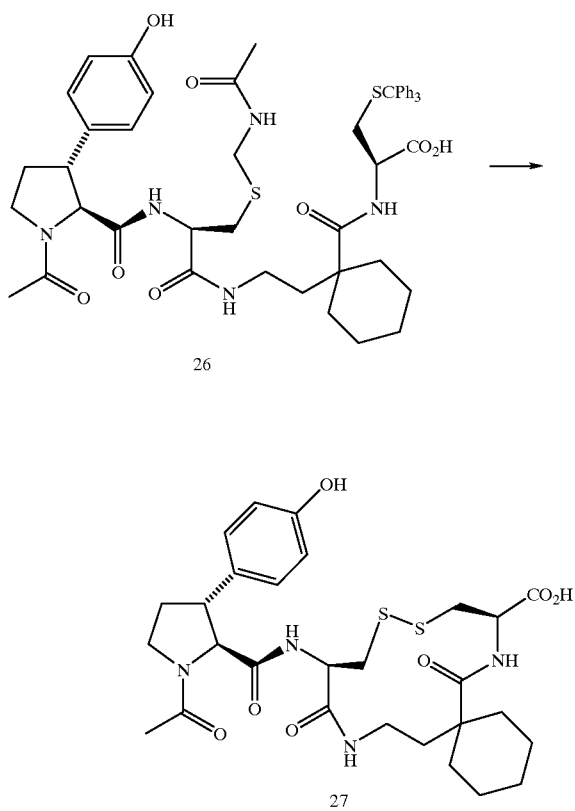

To a solution of 2(R)[[[1-[2-[[3-[[(acetylamino)methyl]thio]-2(R)-[[2(S)3(R)-1-acetyl-3-(4-hydroxyphenyl)pyrrolidin-2-yl]carbonyl]amino]-1-oxopropyl]amino]ethyl]cyclohexyl]carbonyl]amino]-3-[(triplhylmethyl)thio]propanoic acid (26) (40 mg, 0.045 mmole) in CH$_2$Cl$_2$/MeOH (100 ml, 9:1) at room temperature was added dropwise a solution of 12 (41 mg, 0.16 mmole) in CH$_2$Cl$_2$/MeOH (100 ml, 9:1) over 25 min. After the addition was complete, the reaction mixture was stirred for 5 min. and a saturated solution of Na$_2$S$_2$O$_5$ (1 mL) was added dropwise. The reaction mixture was filtered and concentrated under vacuum. Purification by reverse-phase HPLC, using a 15–95% acetonitrile-water gradient over 25 min., provided (9R,14R)-14-[[[1-acetyl-3-(R)-(4-hydroxyphenyl)-2-(S)-pyrrolidinyl]carbony]amino]-7,15-dioxo-11,12-dithia-8,16-diazaspiro[5.12]Octadecane-9-carboxylic acid (6 mg, 23%). High resolution mass spectrum m/z 607.2255 [(M+H)$^+$; Calcd for C$_{28}$H$_{39}$N4O$_7$S$_2$: 607.2260].

EXAMPLE 20

Synthesis of (2S,3R)-3-(4-hydroxyphenyl)pyrrolidine-2-carboxylic Acid methyl Ester hydrochloride

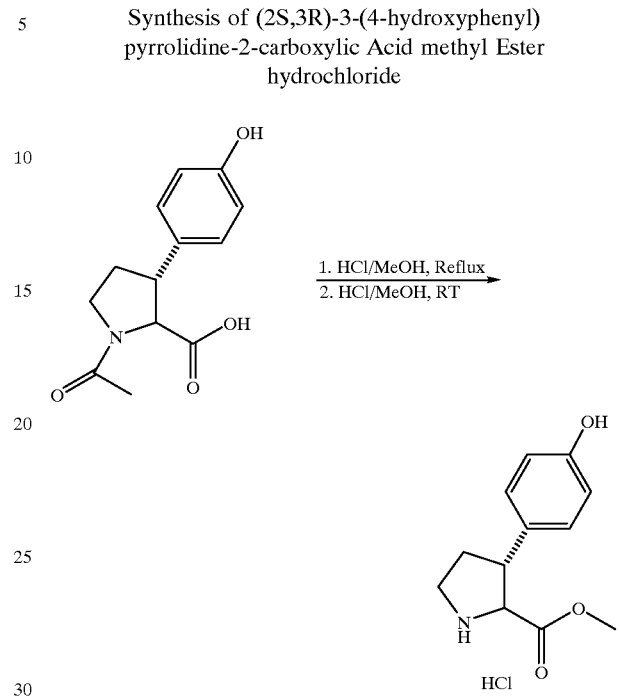

A solution of (2S,3R)-1-acetyl-3-(4-hydroxyphenyl)pyrrolidine-2-carboxylic acid (1.0 g) in 50 mL of methanol was saturated with HCl gas. The solution was refluxed for 24 hours and the solvent was evaporated to give brown solid. This solid was then dissolved in 20 mL of anhydrous saturated HCl in methanol and the resulting solution was stirred overnight at room temperature. After removal the solvent, (2S,3R)-3-(4-hydroxyphenyl)pyrolinidine-2-carboxylic acid methyl ester hydrochloride was obtained as light brown solid (0.83 g).

EXAMPLE 21

Synthesis of (2S,3R)-1-methanesulfonyl-3-(4-hydroxyphenyl)pyrrolidine-2-carboxylic Acid

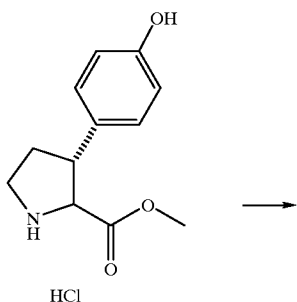

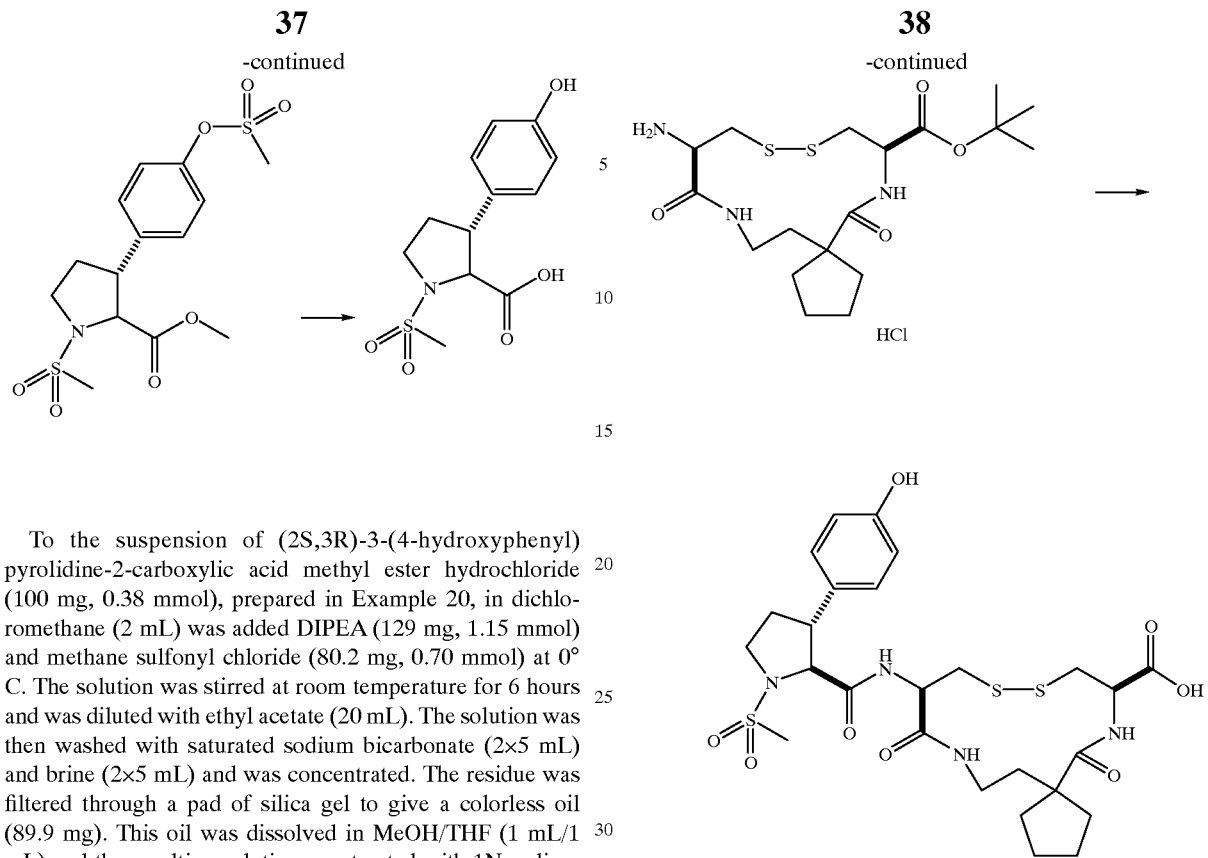

To the suspension of (2S,3R)-3-(4-hydroxyphenyl) pyrolidine-2-carboxylic acid methyl ester hydrochloride (100 mg, 0.38 mmol), prepared in Example 20, in dichloromethane (2 mL) was added DIPEA (129 mg, 1.15 mmol) and methane sulfonyl chloride (80.2 mg, 0.70 mmol) at 0° C. The solution was stirred at room temperature for 6 hours and was diluted with ethyl acetate (20 mL). The solution was then washed with saturated sodium bicarbonate (2×5 mL) and brine (2×5 mL) and was concentrated. The residue was filtered through a pad of silica gel to give a colorless oil (89.9 mg). This oil was dissolved in MeOH/THF (1 mL/1 mL) and the resulting solution was treated with 1N sodium hydroxide (0.5 mL, 0.5 mmol). The solution was stirred at room temperature for 4 hours and was acidified with acetic acid. The crude product was purified by reverse phase HPLC (5–95% of acetonitrile containing 0.75% of TFA in water) over 40 min linear gradient) to give (2S,3R)-1-methanesulfonyl-3-(4-hydroxyphenyl)pyrolidine-2-carboxylic acid as white solid (22 mg, 0.08 mmol). HRMS (M+H): Obs.286.0757, Calcd. 286.0750.

EXAMPLE 22

Synthlesis of (8R,13R)-13-[[[1-methylsulfonyl-3-(R)-(4-hydroxyphenyl)-2-(S)pyrrolidinyl]carbonyl]amino]-6,14-dioxo-10,11-dithia-7,15-diazaspiro[4.12]-heptadecane-8-carboxylic Acid

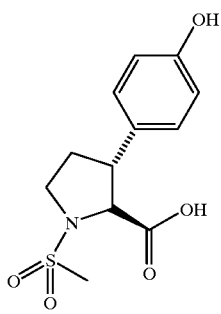

To the mixture of (2S,3R)-1-methanesulfonyl-3-(4-hydroxyphenyl)pyrolidine-2-carboxylic acid (15 mg, 0.05 mmol) and (8R,13R)-13-amino-6,14-dioxo-10,11-dithia-7,15-diazaspiro[4.12]heptadeeane-8-carboxylic acid 1,1-dimethylethyl ester hydrochloride (22.7 mg, 0.05 mmol), prepared in Example 6, in 0.2 mL of DMF was added DIPEA (19.4 mg, 0.15 mmol) and HBTU (19 mg, 0.05 mmol). The solution was stirred at room temperature for 3 hours and was diluted with water to 3 mL. The resulting white precipitate was collected and was dried over night at reduced pressure to give 40 mg of white solid. This dried solid was the dissolved in 1 mL of diehloromethane and the solution was treated with 4 N HCl in dioxane (2 mL). The solution was stirred overnight and was concentrated. The residue was purified by reversed phase HPLC (5–95% of acetonitrile containing 0.75% of TFA in water over a 40 min linear gradient) to give (8R,13 R)-13-[[[1-methylsulfonyl-3-(R)-(4-hydroxyphenyl)-2-(S) pyrrolidinyl]carbonyl]amino]-6,14-dioxo-10,11-dithia-7,15-diazaspiro[4.12]heptadecane-8-carboxylic acid as a white solid (17.3 mg). HRMS (M+H): Obs. 629.1767, Calcd. 629.1773.

EXAMPLE 23

Synthesis of (2S,3R)-1-(2,2-dimethyl-1-oxopropyl)-3-(4-hydroxyphenyl)pyrolidine-2-carboxylic Acid

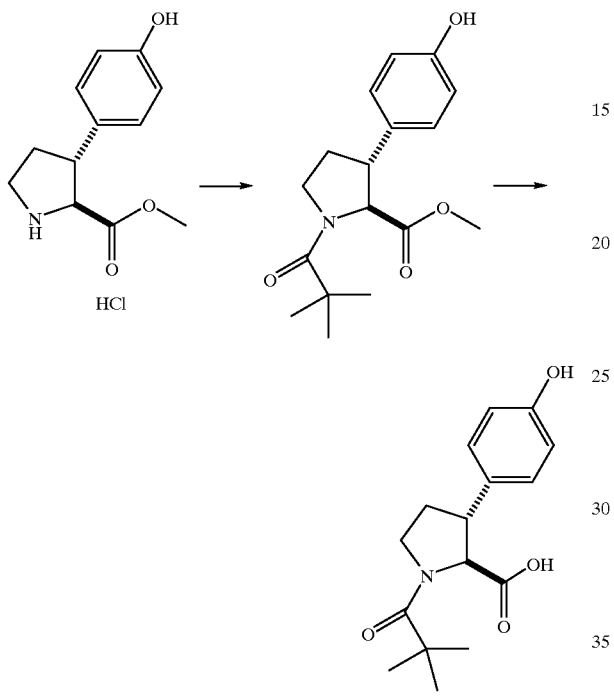

To the solution of (2S,3R)-3-(4-hydroxyphenyl) pyrolidine-2-carboxylic acid methyl ester hydrochloride (200 mg, 0.76 mmol), prepared in Example 20, in THF/H2O (2 mL/1 mL) was added saturated NaHCO$_3$ (5 mL). To the above mixture was added trimethylacetyl chloride (420 mg, 3.5 mmol) over 20 min. The resulting solution was then stirred at room temperature for 4 hours and was diluted with ethyl acetate to 30 mL. The organic layer was then washed with brine (2×5 mL) and was concentrated to give (2S,3R)-1-(1-oxo-2,2,2-trimethylethyl)-3-(4-hydroxyphenyl) pyrolidine-2-carboxylic acid methyl ester as a white solid (320 mg). This solid was dissolved in 3 mL of EtOH and was stirred with 1N sodium hydroxide (3 mL, 3 mmol) at room temperature for 8 hours. After acidification with 6N HCl, the solvent was removed and the residue was extracted with dichloromethane. After concentration, the residue was washed ether to give (2S,3R)-1-(2,2-dimethyl-1-oxopropyl)-3-(4-hydroxyphenyl)pyrolidine-2-carboxylic acid as a white solid (117 mg). HRMS (M+H): Obs. 292.1556, Cald. 292.1549.

EXAMPLE 24

Synthesis of (8R,13R)-13-[[[1-(2,2-dimethyl-1-oxopropyl)-3(R)-(4-hydroxyphenyl)-2(S)-pyrrolidinyl]carbonyl]amino]-6,14-dioxo-10,11-dithia-7,15-diazaspiro[4.12]heptadecane-8-carboxylic Acid

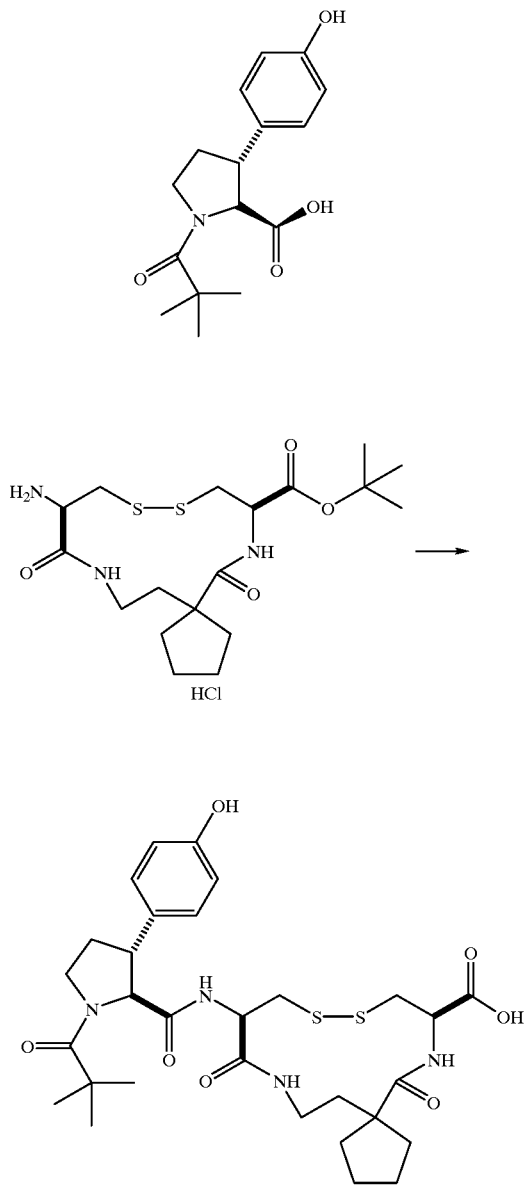

To a mixture of (2S,3R)-1-(2,2-dimethyl-1-oxopropyl)-3-(4-hydroxyphenyl)pyrolidine-2-carboxylic acid (45 mg, 0.15 mmol) and (8R,13R)-13-amino-6,14-dioxo-10,11-dithia-7,15-diazaspiro[4.12]heptadecane-8-carboxylic acid 1,1-dimethylethyl ester hydrochloride 70 mg, 0.15 mmol), prepared in Example 6, in 0.5 mL of DMF was added DIPEA (58 mg, 0.45 mmol) and HBTU (59 mg, 0.15 mmol). The solution was stirred at room temperature for 3 hours and was diluted with water to 3 mL. The resulting white precipitate was collected and was dried over night at reduced pressure to give 98 mg of (8R,13R)-13-[[[1-(2,2-dimethyl-1-oxopropyl)-3-(R)-(4-hydroxyphenyl)-2-(S)-pyrrolidinyl]carbonyl]amino]-6,14-dioxo-10,11-dithia-7,15-diazaspiro

[4.12]heptadecane-8-carboxylic acid 1,1-dimethylethyl ester as a white solid. This dried solid was the dissolved in 1 mL of dichloromethane and the solution was treated with 4 N HCl in dioxane (2 mL). The solution was stirred overnight and was concentrated. The residue was purified by reversed phase HPLC (5–95% of acetonitrile containing 0.75% of TFA in water over 40 min linear gradient) to give (8R,13R)-13-[[[1-(2,2-dimethyl-1-oxopropyl)-3(R)-(4-hydroxyphenyl)-2(S)-pyrrolidinyl]carbonyl]amino]-6,14-dioxo-10,11-dithia-7,15-diazaspiro[4.12]heptadecane-8-carboxylic acid as white solid (9 mg). HRMS (M+H): Obs. 635.2543, Calcd. 635.2573.

EXAMPLE 25

Synthesis of (2S,3R)-1-[(1,1-dimethylethoxyl)carbonyl]-3-(4-hydroxyphenyl)-pyrolidine-2-carboxylic Acid

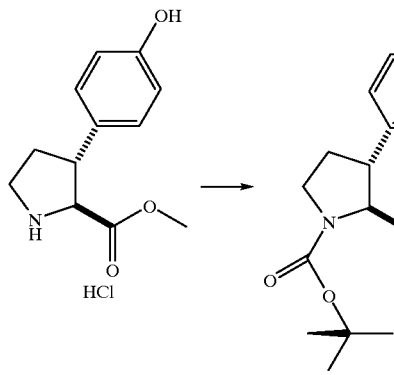

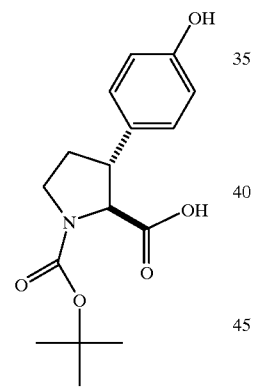

To the suspension of (2S,3R)-3-(4-hydroxyphenyl)pyrolidine-2-carboxylic acid methyl ester hydrochloride (100 mg, 0.38 mmol), prepared in Example 20, in THF (2 mL) was added DIPEA (65 mg, 0.5 mmol) and Boc$_2$O (218 mg, 1 mmol) at 20° C. The solution was then stirred at room temperature for 16 hours and was diluted with ethyl acetate (20 mL). The solution was then washed with saturated sodium bicarbonate (2×5 mL) and brine (2×5 mL) and was concentrated. The residue was filtered through silica gel to give (2S,3R)-1-[(1,1-dimethylethoxyl)carbonyl]-3-(4-hydroxyphenyl)pyrolidine-2-carboxylic acid methyl ester as a colorless oil (113 mg). This oil was then dissolved in MeOH/THF (2 mL/1 mL) and the resulting solution was treated with 1N sodium hydroxide (0.7 mL, 0.7 mmol). The solution was stirred at room temperature for 4 hours. and was acidified with acetic acid. The crude product was purified by reverse-phase HPLC (5–95% of acetonitrile containing 0.75% of TFA in water over 40 min linear gradient) to give (2S,3R)-1-[(1,1-dimethylethoxyl)carbonyl]-3-(4-hydroxyphenyl)pyrrolidine-2-carboxylic acid as white solid (70 mg, 0.22 mmol). HRMS (M+H): Obs. 308.1511, Calcd. 308.1498.

EXAMPLE 26

Synthesis of (8R,13R)-13-[[[3(R)-(4-hydroxyphenyl)-2(S)-pyrrolidinyl]carbonyl]-amino]-6,14-dioxo-10,11-dithia-7,15-diazaspiro[4.12]heptadecane-8-carboxylic Acid

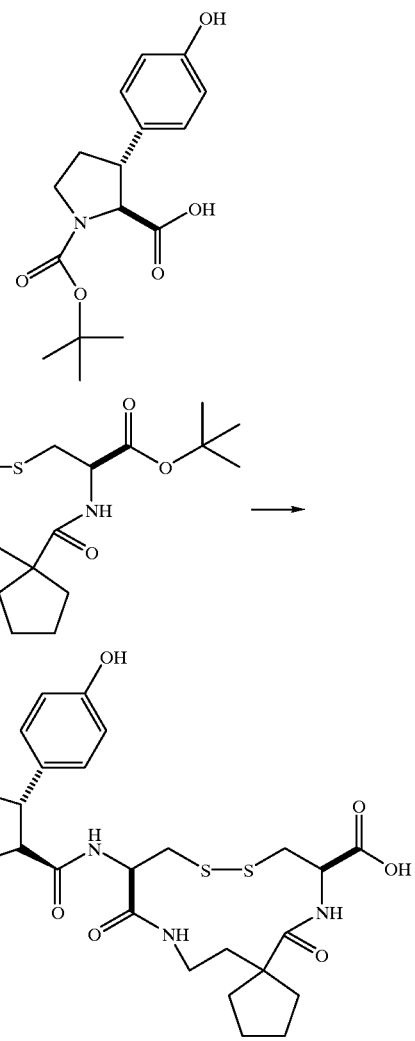

To the mixture of (2S,3R)-1-[(1,1-dimethylethoxy)carbonyl]-3-(4-hydroxyphenyl)pyrrolidine-2-carboxylic acid (46 mg, 0.15 mmol) and (8R,13R)-13-amino-6,14-dioxo-10,11-dithia-7,15-diazaspiro[4.12]heptadecane-8-carboxylic acid 1,1-dimethylethyl ester hydrochloride 70 mg, 0.15 mmol), prepared in Example 6, in 0.5 mL of DMF was added DIPEA (58 mg, 0.45 mmol) and HBTU (59 mg, 0.15 mmol). The solution was stirred at room temperature for 3 hours and was diluted with water to 3 mL. The resulting white precipitate was collected and was dried over night at reduced pressure to give 105 mg of (8R,13R)-13-[[[3(R)-(4-hydroxyphenyl)-2(S)-pyrrolidinyl]carbonyl]amino]-6,14-dioxo-10,11-dithia-7,15-diazaspiro[4.12]heptadecane-8-carboxylic acid 1,1-dimethylethyl ester as a white solid. This dried solid (85 mg) was the dissolved in 2 mL of dichloromethane and the solution was treated with 4 N HCl in dioxane (2 mL). The solution was stirred overnight and the solvent was then removed. The residue was purified by reversed-phase HPLC (5–95% of acetonitrile containing 0.75% of TFA in water oevr 40 min linear gradient) to give (8R,13R)-13-[[[3(R)-(4-hydroxyphenyl)-2(S)-pyrrolidinyl]carbonyl]amino]-6,14-dioxo-10,11-dithia-7,15-diazaspiro[4.12]heptadecane-8-carboxylic acid as a white solid (58 mg). HRMS (M+H): Obs. 551.2017, Calcd.551.1998.

EXAMPLE 27

VLA-4/VCAM-1 Screening Assay

VLA-4 antagonist activity, defined as ability to compete for binding to immobilized VCAM-1, was quantitated using a solid-phase, dual antibody ELISA. VLA-4 ($\alpha 4\beta 1$ integrin) bound to VCAM-1 is detected by a complex of anti-integrin $\beta 1$ antibody: HRP-conjugated anti-mouse IgG: chromogenic substrate (K-Blue). Initially, this entailed coating 96 well plates (Nunc Maxisorp) with recombinant human VCAM-1 (0.4 $\mu$g in 100 $\mu$l PBS), sealing each plate and then allowing the plates to stand at 4° C. for 18 hours. The VCAM-coated plates were subsequently blocked with 250 $\mu$l of 1% BSA/0.02% NaN$_3$ to reduce non-specific binding. On the day of assay, all plates are washed twice with VCAM Assay Buffer (200 $\mu$l/well of 50 mM Tris-HCl, 100 mM NaCl, 1 mM MnCl$_2$, 0.05% T ween 20; pH 7.4). Test compounds are dissolved in 100% DMSO and then diluted 1:20 in VCAM Assay Buffer supplemented with 1 mg/mL BSA (i.e., final DMSO=5%). A series of 1:4 dilutions are performed to achieve a concentration range of 0.005 nM–1.563 $\mu$M for each test compound. 100 $\mu$l per well of each dilution is added to the VCAM-coated plates, followed by 10 $\mu$l of Ramos cell-derived VLA-4. These plates are sequentially mixed on a platform shaker for 1 min, incubated for 2 hour at 37° C., and then washed four times with 200 $\mu$l/well VCAM Assay Buffer. 100 $\mu$l of mouse anti-human integrin b1 antibody is added to each well (0.6 $\mu$g/mL in VCAM Assay Buffer+1 mg/mL BSA) and allowed to incubate for 1 hour at 37° C. At the conclusion of this incubation period, all plates are washed four times with VCAM Assay Buffer (200 $\mu$l/well). A corresponding second antibody, HRP-conjugated goat anti-mouse IgG (100 $\mu$l per well @ 1:800 dilution in VCAM Assay Buffer+1 mg/mL BSA), is then added to each well, followed by a 1 hour incubation at room temperature and concluded by three washes (200 $\mu$l/well) with VCAM Assay Buffer. Color development is initiated by addition of 100 $\mu$l K-Blue per well (15 mim incubation, room temp) and terminated by addition of 100 $\mu$l Red Stop Buffer per well. All plates are then read in a UV/Vis spectrophotometer at 650 nM. Results are calculated as % inhibition of total binding (i.e., VLA-4+VCAM-1 in the absence of test compound).

EXAMPLE 28

Ramos (VLA-4)/VCAM-1 Cell-Based Screening Assay Protocol

Materials:

Soluble recombinant human VCAM-1 (mixture of 5- and 7-Ig domain) was purified from CHO cell culture media by immunoaffinity chromatography and maintained in a solution containing 0.1 M Tris-glycine (pH 7.5), 0.1 M NaCl, 5 mM EDTA, 1 mM PMSF, 0.02% 0.02% NaN$_3$ and 10 $\mu$g/mL leupeptin. Calcein-AM was purchased from Molecular Probes Inc.

Methods:

VLA-4 (a4b1 integrin) antagonist activity, defined as the ability to compete with cell-surface VLA-4 for binding to immobilized VCAM-1, was quantitated using a Ramos-VCAM-1 cell adhesion assay. Ramos cells bearing cell-surface VLA-4, were labeled with a fluorescent dye (Calcein-AM) and allowed to bind VCAM-1 in the presence or absence of test compounds. A reduction in fluorescence intensity associated with adherent cells (% inhibition) reflected competitive inhibition of VLA-4 mediated cell adhesion by the test compound.

Initially, this entailed coating 96 well plates (Nunc Maxisorp) with recombinant human VCAM-1 (100 ng in 100 $\mu$l PBS), sealing each plate and allowing the plates to stand at 4° C. for ~18 hour. The VCAM-coated plates were subsequently washed twice with 0.05% Tween-20 in PBS, and then blocked for 1 hour (room temperature) with 200 $\mu$l of Blocking Buffer (1% BSA/0.02% thimerosal) to reduce non-specific binding. Following the incubation with Blocking Buffer, plates were inverted, blotted and the remaining buffer aspirated. Each plate was then washed with 300 $\mu$l PBS, inverted and the remaining PBS aspirated.

Test compounds were dissolved in 100% DMSO and then diluted 1:25 in VCAM Cell Adhesion Assay Buffer (4 mM CaCl$_2$, 4 mM MgCl$_2$ in 50 mM TRIS-HCl, pH 7.5) (final DMSO=4%). A series of eight 1:4 dilutions were performed for each compound (general concentration range of 1 nM–12,500 nM). 100 $\mu$l/well of each dilution was added to the VCAM-coated plates, followed by 100 $\mu$l of Ramos cells (200,000 cells/well in 1% BSA/PBS). Plates containing test compounds and Ramos cells were allowed to incubate for 45 min at room temperature, after which 165 $\mu$l/well PBS was added. Plates were inverted to remove non-adherent cells, blotted and 300 $\mu$l/well PBS added. Plates were again inverted, blotted and the remaining buffer gently aspirated. 100 $\mu$l Lysis Buffer (0.1% SDS in 50 mM TRIS-HCl, pH 8.5) was added to each well and agitated for 2 min on a rotary shaking platform. The plates were then read for fluorescence intensity on a Cytofluor 2300 (Millipore) fluorecence measurement system (excitation=485 nm, emission=530 nm).

| Compound from Example | Elisa Assay IC$_{50}$ nM | Ramos Cell Assay IC$_{50}$ nM |
|---|---|---|
| TBC772 | 227 | 1,800 |
| 12 | 0.185 | 0.21 |
| 24 | 0.14 | 0.18 |
| 26 | 0.19 | 0.15 |
| 22 | 0.17 | 0.32 |
| 19 | 0.12 | 0.28 |
|  | 1.65 | 24 |

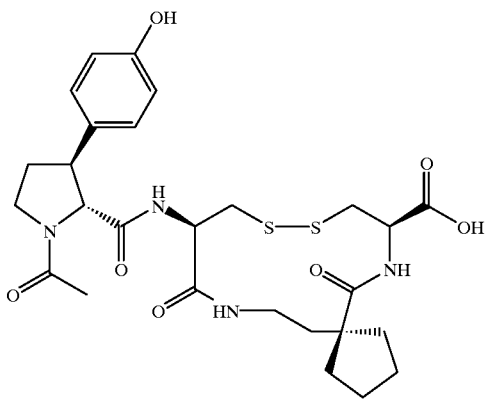

What is claimed is:

1. A compound of the formula:

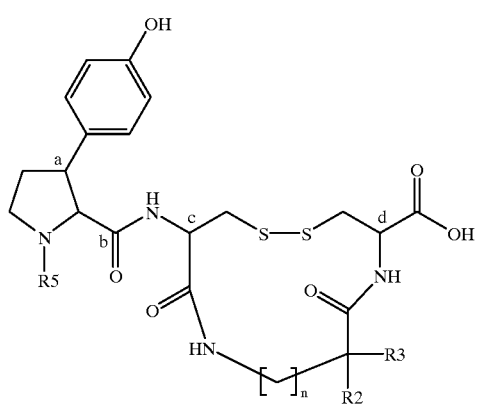

I or hydrolyzable organic esters or ethers thereof; wherein

R$_2$ and R$_3$ are each independently lower alkyl, or taken together with their attached carbon atom form an aliphatic carbocyclic ring containing 4 to 6 carbon atoms;

R$_5$ is hydrogen, lower alkyl, R—SO$_2$—, R$_6$—(CH2)$_m$—CO— or R$_8$—X—(CH2)$_y$—CO—, wherein R is lower alkyl, R$_6$ and R$_8$ are hydrogen or lower alkyl, X is —O— or —NH—, m is an integer of from 1 to 7 and y is an integer of from 0 to 7;

n is an integer of from 1 to 3; and a, b, c, and d denote asymmetric carbon atoms.

2. The compound of claim 30 wherein, R$_2$ and R$_3$ together with their attached carbon form an aliphatic cycloalkane ring.

3. The compound of claim 2, wherein R$_2$ and R$_3$ together with their attached carbon form a cyclopentane ring.

4. The compound of claim 3, wherein the compound has the formula

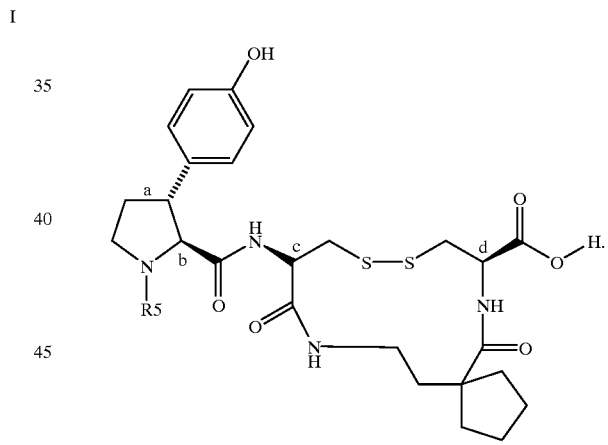

5. The compound of claim 4, wherein said compound is (8R,13R)-13-[[[3-(R)-(4-hydroxyphenyl)-2-(S)-pyrrolidinyl]carbonyl]amino]-6,14-dioxo-10,11-dithia-7,15-diazaspiro[4.12]heptadecane-8-carboxylic acid.

6. The compound of claim 4 wherein R$_5$ is R$_6$—(CH$_2$)$_m$CO—.

7. The compound of claim 6 wherein said compound is (8R,13R)-13-[[[1-acetyl-3-(R)-(4-hydroxyphenyl)-2-(S)-pyrrolidinyl]carbonyl]amino]-6,14-dioxo-10,11-dithia-7,15-diazaspiro[4.12]heptadecane-8-carboxylic acid.

8. The compound of claim 6, wherein said compound is (8R,13R)-13-[[[1-(2,2-dimethyl-1-oxopropyl)-3-(R)-(4-hydroxyphenyl)-2-(S)-pyrrolidinyl]carbonyl]amino]-6,14-dioxo-10,11-dithia-7,15-diazaspiro[4.12]heptadecane-8-carboxylic acid.

9. The compound of claim 4, wherein $R_5$ is $R_8$—X—$(CH_2)_y$—CO—.

10. The compound of claim 9, wherein X is oxygen.

11. The compound of claim 4, wherein $R_5$ is hydrogen.

12. The compound of claim 11, wherein said compound is (8R,13R)-13-[[[3-(R)-(4-hydroxyphenyl)-2-(S)-pyrrolidinyl]carbonyl]amino]-6,14-dioxo-10,11-dithia-7,15-diazaspiro[4.12]heptadecane-8-carboxylic acid.

13. The compound of claim 4, wherein $R_5$ is R—$SO_2$—.

14. The compound of claim 4, wherein $R_5$ is lower alkyl.

15. The compound of claim 13, wherein said compound is (8R,13R)-13-[[[1-methylsulfonyl-3(R)-(4-hydroxyphenyl)-2(S)pyrrolidinyl]carbonyl]amino]-6,14-dioxo-10,11-dithia-7,15-diazaspiro[4.12]heptadecane-8-carboxylic acid.

16. The compound of claim 2, wherein $R_2$ and $R_3$ together with their attached carbon form a cyclohexane ring.

17. The compound of claim 16, wherein the compound has the formula:

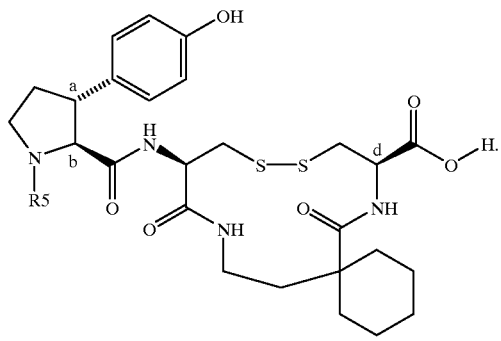

18. The compound of claim 17, wherein said compound is (9R,14R)-14-[[[3-(R)-(4-hydroxyphenyl)-2-(S)-pyrrolidinyl]carbonyl]amino]-7,15-dioxo-11,12-dithia-8,16-diazaspiro[5.12]octadecane-9-carboxylic acid.

19. The compound of claim 17, wherein $R_5$ is $R_6$—$(CH_2)_m$—CO—.

20. The compound of claim 19 wherein said compound is (9R,14R)-14-[[[1-acetyl-3-(R)-(4-hydroxyphenyl)-2-(S)-pyrrolidinyl]carbonyl]amino]-7,15-dioxo-11,12-dithia-8,16-diazaspiro[5.12]Octadecane-9-carboxylic acid.

21. A compound selected from the group consisting of compound of the formula

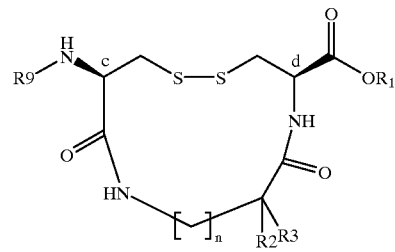

wherein $R_1$ with its attached oxygen forms a hydrolyzable ester group; $R_2$ and $R_3$ are each independently lower alkyl, or taken together with their attached carbon atom form an aliphatic carbocyclic ring containing 4 to 6 carbon atoms; $R_9$ is an amino protecting group; and n is an integer of from 1 to 3.

22. The compound of claim 21, wherein $R_2$ and $R_3$ together with their attached carbon form a cyclopentane ring.

23. The compound of claim 22, which is (8R,13R)-13-[[(1,1-dimethylethoxy]carbonyliamino]-6,14-dioxo-10,11-dithia-7,15-diazaspiro[4.12]heptadecane-8-carboxylic acid 1,1-dimethylethyl ester.

24. A compound selected from the group consisting of compound of the formula

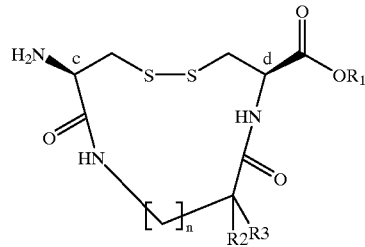

wherein $R_1$ with its attached oxygen forms a hydrolyzable ester group; $R_2$ and $R_3$ are each independently lower alkyl, or taken together with their attached carbon atom form an aliphatic carbocyclic ring containing 4 to 6 carbon atoms; and n is an integer of from 1 to 3.

25. The compound of claim 24, wherein $R_2$ and $R_3$ together with their attached carbon form a cyclopentane ring.

26. The compound of claim 25, which is (8R,13R)-13-amino-6,14-dioxo-10,11-dithia-7,15-diazaspiro[4.12]heptadecane-8-carboxylic acid 1,1-dimethylethyl ester.

\* \* \* \* \*

UNITED STATES PATENT AND TRADEMARK OFFICE
CERTIFICATE OF CORRECTION

PATENT NO.   : 6,265,572 B1
DATED        : July 24, 2001
INVENTOR(S)  : Li Chen et al.

It is certified that error appears in the above-identified patent and that said Letters Patent is hereby corrected as shown below:

<u>Column 45, claim 2,</u>
Line 63, delete "claim 30" and insert therefor -- claim 1 --

Signed and Sealed this

Nineteenth Day of March, 2002

Attest:

Attesting Officer

JAMES E. ROGAN
*Director of the United States Patent and Trademark Office*